US009750521B2

(12) United States Patent
Lamping et al.

(10) Patent No.: US 9,750,521 B2
(45) Date of Patent: Sep. 5, 2017

(54) ULTRASONIC BLADE OVERMOLD

(71) Applicant: Ethicon Endo-Surgery, Inc., Cincinnati, OH (US)

(72) Inventors: Michael R. Lamping, Cincinnati, OH (US); David A. Witt, Maineville, OH (US); Matthew D. Holcomb, Lebanon, OH (US); Nabeel M. Jadeed, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 22 days.

(21) Appl. No.: 14/337,508

(22) Filed: Jul. 22, 2014

(65) Prior Publication Data

US 2016/0022305 A1    Jan. 28, 2016

(51) Int. Cl.
*A61B 17/32*   (2006.01)
*A61B 17/00*   (2006.01)

(52) U.S. Cl.
CPC ......... *A61B 17/320068* (2013.01); *A61B 2017/00526* (2013.01); *A61B 2017/320088* (2013.01)

(58) Field of Classification Search
CPC ...... A61B 17/22004; A61B 17/320068; A61B 17/320092; A61B 2017/320088
See application file for complete search history.

(56) References Cited

U.S. PATENT DOCUMENTS

| | | | |
|---|---|---|---|
| 4,834,080 A * | 5/1989 | Brown | A61B 17/1753 606/96 |
| 5,322,055 A | 6/1994 | Davison et al. | |
| 5,324,299 A | 6/1994 | Davison et al. | |
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |

(Continued)

FOREIGN PATENT DOCUMENTS

WO    WO 98/37815 A1    9/1998
WO    WO 2007/047380 A2    4/2007

(Continued)

OTHER PUBLICATIONS

U.S. Appl. No. 14/028,717, filed Sep. 17, 2013.

(Continued)

*Primary Examiner* — Todd J Scherbel
(74) *Attorney, Agent, or Firm* — Frost Brown Todd LLC

(57) ABSTRACT

An ultrasonic instrument comprises an ultrasonic transducer, an acoustic waveguide, and an ultrasonic blade. The acoustic waveguide comprises a bore extending through the waveguide, an anchor pin, and an acoustic isolator. The anchor pin is insertable through the bore and is operable to longitudinally anchor the acoustic waveguide relative to the ultrasonic instrument. The acoustic isolator is radially disposed about the acoustic waveguide and is operable to acoustically isolate the acoustic waveguide from the ultrasonic instrument. The acoustic isolator comprises an opening extending through the isolator. The opening is configured to receive the anchor pin. The ultrasonic blade is in acoustic communication with the acoustic waveguide such that the ultrasonic transducer is operable to drive the ultrasonic blade to vibrate ultrasonically via the acoustic waveguide.

20 Claims, 20 Drawing Sheets

(56) References Cited

U.S. PATENT DOCUMENTS

| | | | |
|---|---|---|---|
| 6,423,082 | B1 | 7/2002 | Houser et al. |
| 6,773,444 | B2 | 8/2004 | Messerly |
| 6,783,524 | B2 | 8/2004 | Anderson et al. |
| 8,057,498 | B2 | 11/2011 | Robertson |
| 8,152,825 | B2 | 4/2012 | Madan et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,911,460 | B2 | 12/2014 | Neurohr et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0069940 | A1 | 3/2010 | Miller et al. |
| 2011/0087212 | A1 | 4/2011 | Aldridge et al. |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0114334 | A1 | 4/2014 | Olson et al. |

FOREIGN PATENT DOCUMENTS

| | | |
|---|---|---|
| WO | WO 2008/089174 A2 | 7/2008 |
| WO | WO 2015/094746 A1 | 6/2015 |

OTHER PUBLICATIONS

U.S. Appl. No. 14/031,665, filed Sep. 19, 2013.
U.S. Appl. No. 61/410,603, filed Nov. 5, 2010.
International Search Report and Written Opinion dated Sep. 25, 2015 for Application No. PCT/US2015/040851, 14 pgs.

\* cited by examiner

ULTRASONIC BLADE OVERMOLD

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued on Jul. 16, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued on Aug. 4, 2015, the disclosure of which is incorporated by reference herein.

Acoustic waveguides may be equipped with a plurality of elastomeric isolators to isolate the waveguide from other components of the surgical instrument such as sheaths, covers, or other mating parts. Such isolators reduce transfer of ultrasonic energy to other parts of the surgical instrument to aid user comfort and grip, and reduce wear on parts that may contact waveguide. To further reduce transfer of ultrasonic energy, isolators may be positioned at acoustic nodes along the waveguide (i.e., at positions along the length of the waveguide corresponding to nodes associated with resonant ultrasonic vibrations communicated through the waveguide).

To anchor the waveguide to a body of the surgical instrument, a pin or plurality of pins may be inserted through the mating components and into the waveguide. Such pins may also be placed at acoustic nodes to reduce transfer of ultrasonic energy from the waveguide to other components that are in contact with the pins. In some instances it may be desirable to place an isolator and a pin at the same nodal position. While such placement may be preferred, limitations on design and manufacturing processes may make such placement difficult because of the isolator interfering with the placement of the pin. Accordingly, there may be a need for a pin and isolator to share the same nodal position without interfering with each other.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
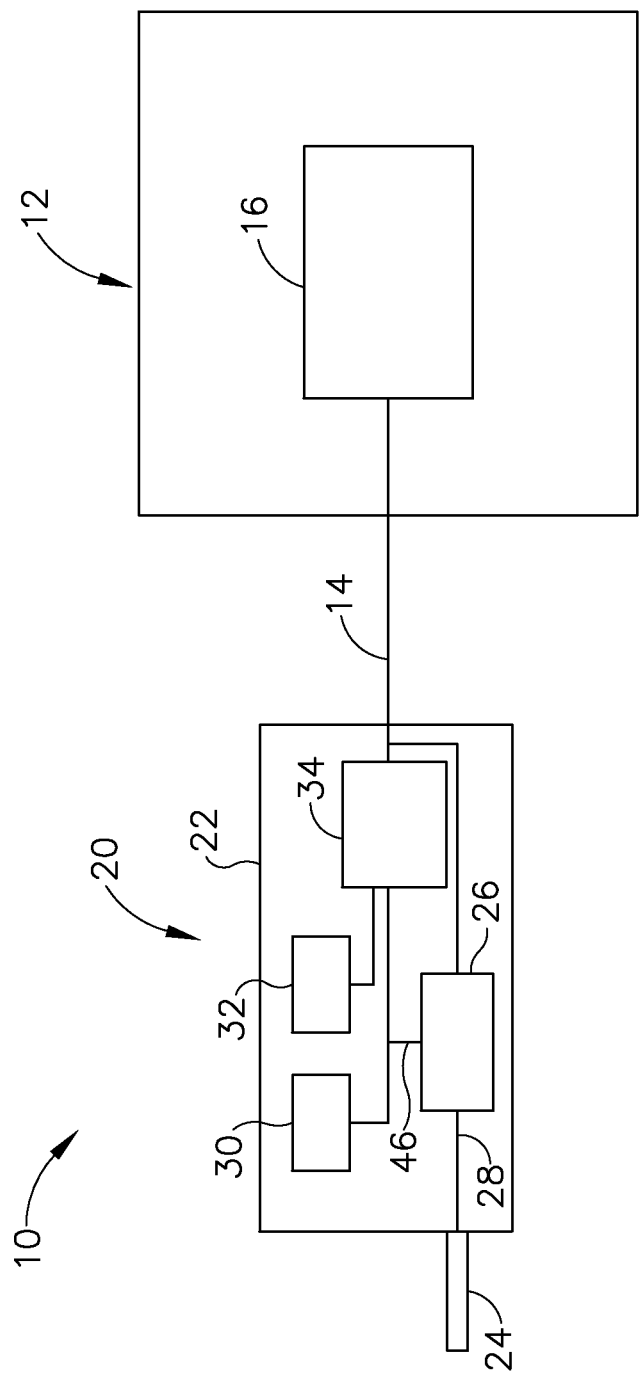
FIG. 1 depicts a block schematic view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04 or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No.

8,986,302, issued on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes HF105 and DH105 by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instruments

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-9 illustrate exemplary ultrasonic surgical instruments (120, 220, 320). At least part of each instrument (120, 220, 320) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S. Pat. No. 9,393,037, issued on Jul. 16, 2016; U.S. Pat. Pub. No. 2014/0114334, now U.S. Pat. No. 9,095,367, issued on Aug. 4, 2015; U.S. patent application Ser. No. 14/028,717, published as U.S. Pub. No. 2015/0080924 on Mar. 19, 2015; and/or U.S. Pat. App. No. 61/410,603. The disclosures of each of the foregoing patents, publications, and applications are incorporated by reference herein. As described therein and as will be described in greater detail below, each instrument (120, 220, 320) is operable to cut tissue and seal or weld tissue (e.g., a blood vessel, etc.) substantially simultaneously. It should also be understood that instruments (120, 220, 320) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (120, 220, 320) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (120, 220, 320), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
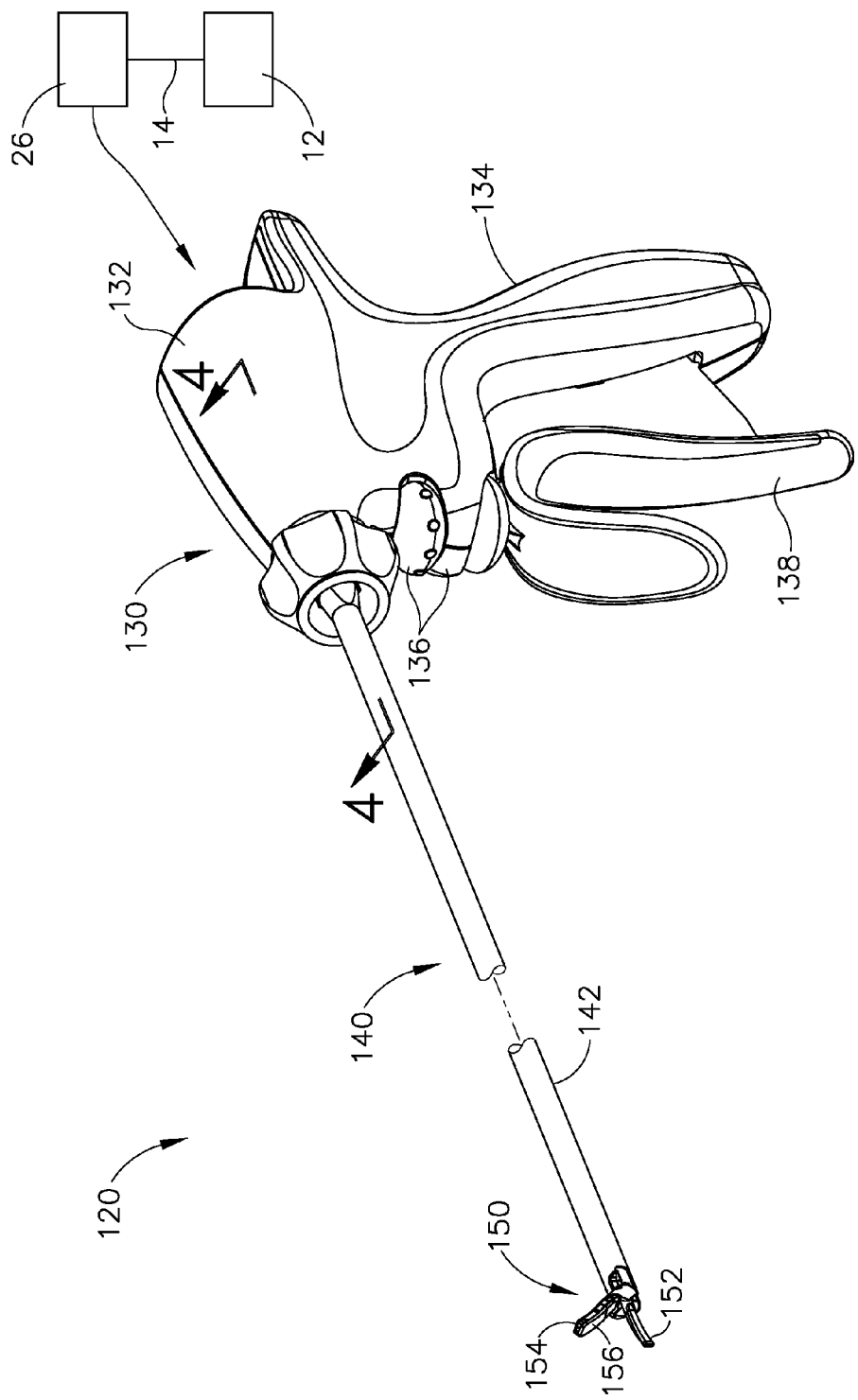
FIG. 2 depicts a perspective view of an exemplary surgical instrument for use with the ultrasonic surgical system of FIG. 1.
Figure 3:
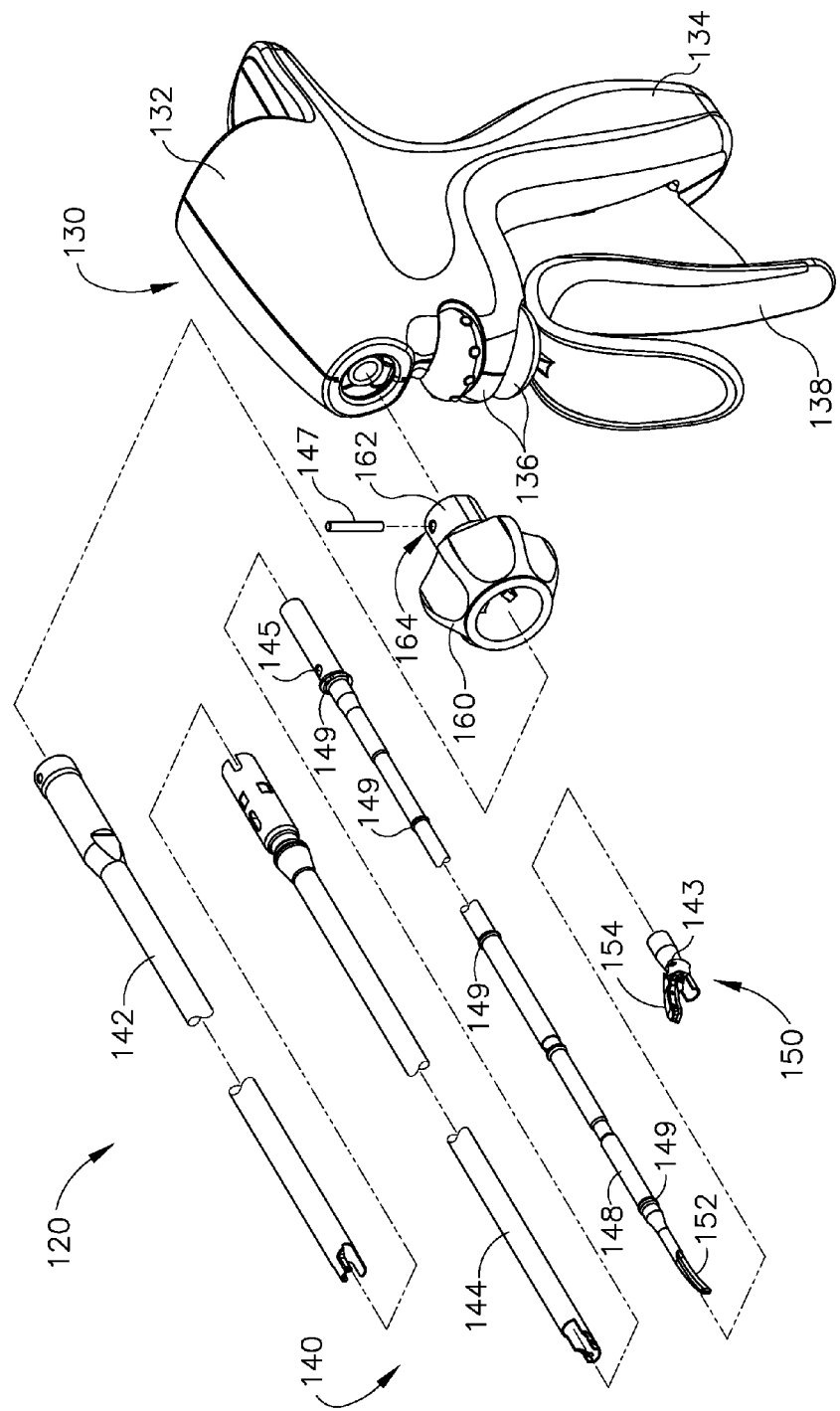
FIG. 3 depicts a partially exploded perspective view of the surgical instrument of FIG. 2.
Figure 4:
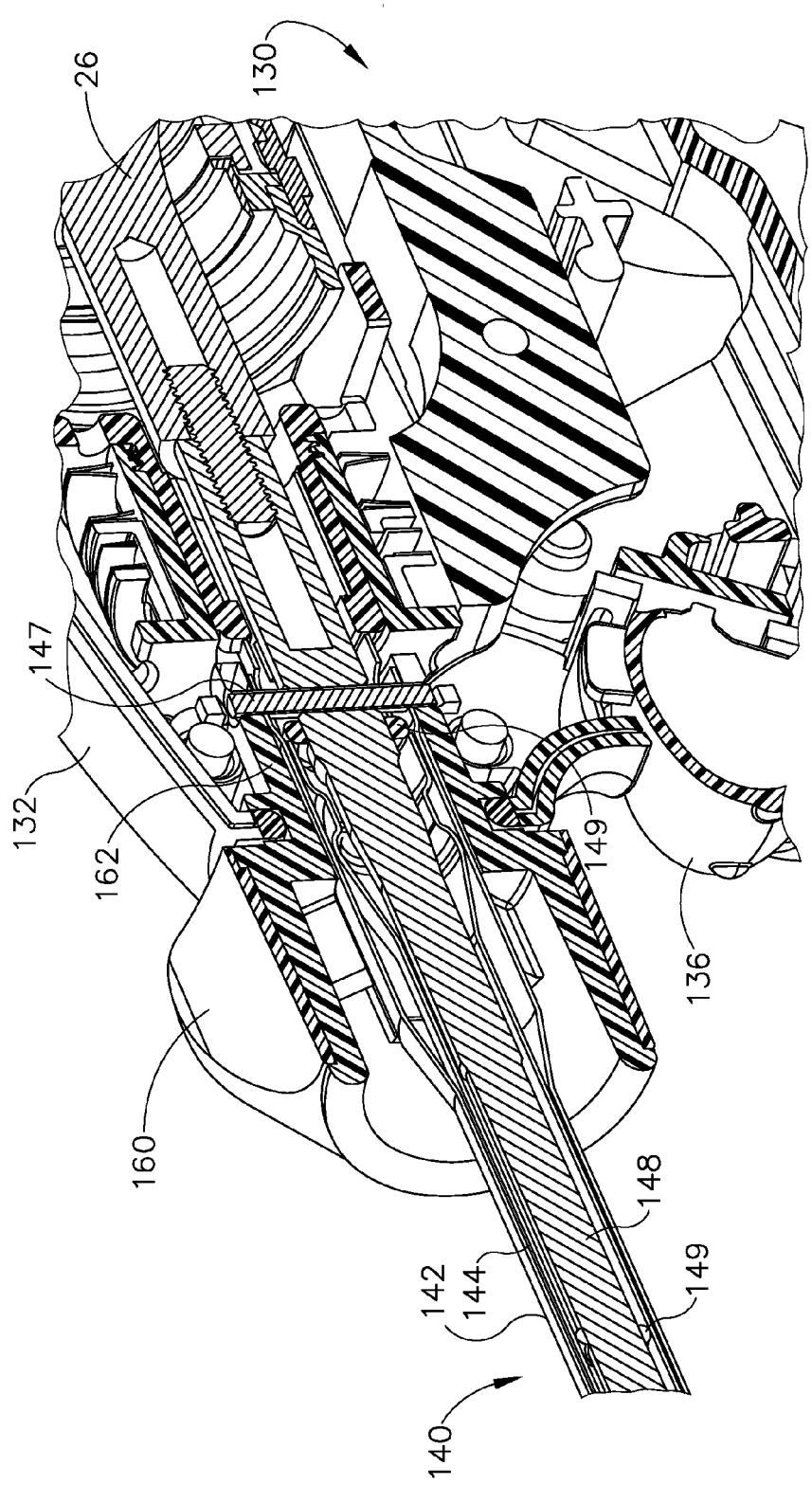
FIG. 4 depicts a perspective cross-sectional view of the surgical instrument of FIG. 2, with the cross-section taken along line 4-4 of FIG. 2.

A. Exemplary Ultrasonic Surgical Instrument for Minimally Invasive Surgical Procedures FIGS. 2-4 depict an exemplary ultrasonic surgical instrument (120) that is configured to be used in minimally invasive surgical procedures (e.g., via a trocar or other small diameter access port, etc.). Instrument (120) of the present example may be used in conjunction with surgical system (10) of FIG. 1, which that includes ultrasonic transducer (26) coupled with ultrasonic generator (12) via cable (14). Instrument (120) comprises a handle assembly (130), a shaft assembly (140) and an end effector (150). In some versions, handle assembly (130) may receive ultrasonic transducer (26) which may couple to a waveguide (148) in shaft assembly (140) by a threaded connection, though any other suitable type of coupling may be used. As shown in FIG. 3, shaft assembly (140) comprises an outer sheath (142), an inner tube (144) slidably disposed within outer sheath (142), and a waveguide (148) disposed within inner tube (144). As will be discussed in greater detail below, longitudinal translation of inner tube (144) relative to outer sheath (142) causes actuation of clamp arm (154) at end effector (150). Handle assembly (130) comprises a body (132) including a pistol grip (134) and a pair of buttons (136). Handle assembly (130) also includes a trigger (138) that is pivotable toward and away from pistol grip (134). It should be understood, however, that various other suitable configurations may be used, including but not limited to a scissor grip configuration. In the present example, a resilient member biases trigger (138) away from pistol grip (134). Trigger (138) is pivotable toward pistol grip (134) to drive inner tube (144) proximally relative to outer sheath (142). When trigger (138) is thereafter released or driven away from pistol grip (134), inner tube (144) is driven distally relative to outer sheath (142). By way of example only, trigger (138) may be coupled with inner tube (144) in accordance with the teachings of various references cited herein. Other suitable ways in which trigger (138) may be coupled with inner tube (144) will be apparent to those of ordinary skill in the art in view of the teachings herein.

Shaft assembly (140) is shown as comprising outer sheath (142), inner tube (144), and waveguide (148) with end effector (150) disposed distally of shaft assembly (140). In some examples, shaft assembly (140) may be attached to a rotation member (160) which may permit shaft assembly (140) to rotate relative to handle assembly (130). In particular, rotation member (160) may be actuated by a user to rotate the entire shaft assembly (140) to thereby rotate end effector (150) relative to handle assembly (130). It should be understood that in examples with a rotatable shaft assembly (140), waveguide (148) may remain coupled to transducer (26) during rotation such that waveguide (148) may be energized even when shaft assembly (140) is being rotated. In other examples, such functionality may be omitted and rotation of shaft assembly (140) may prevent waveguide (148) from being energized. Yet in other examples, rotation member (160) may be omitted entirely and shaft assembly (140) may be fixed relative to handle assembly (130).

As shown in FIGS. 2-3, end effector (50) includes an ultrasonic blade (152) and a pivoting clamp arm (154). Clamp arm (154) includes a clamp pad (156) facing ultrasonic blade (152). Clamp arm (154) is pivotably coupled with a distal end of outer sheath (142) of shaft assembly (140), above ultrasonic blade (152), via a pin (143). A distal end of inner tube (152) is pivotably coupled with a proximal end of clamp arm (154), below ultrasonic blade (152), via another pin (not shown). Thus, longitudinal translation of inner tube (144) relative to outer sheath (142) causes clamp arm (154) to pivot about pin (143) toward and away from ultrasonic blade (152) to thereby clamp tissue between clamp pad (156) and ultrasonic blade (152) to transect and/or seal the tissue. In particular, proximal longitudinal translation of inner tube (144) relative to outer sheath (142) and handle assembly (130) causes clamp arm (154) to pivot toward ultrasonic blade (152); and distal longitudinal translation of inner tube (144) relative to outer sheath (142) and handle assembly (130) causes clamp arm (154) to pivot away from ultrasonic blade (152). It should therefore be understood that pivoting of trigger (138) toward pistol grip (134) will cause clamp arm (154) to pivot toward ultrasonic blade (152); and that pivoting of trigger (138) away from pistol grip (134) will causes clamp arm (154) to pivot away from ultrasonic blade (152).

Ultrasonic transducer (26) may be received within the proximal end of body (132) of handle assembly (130). As described above, transducer (26) is coupled with a generator (12) via a cable (14). Transducer (26) receives electrical power from generator (12) and converts that power into ultrasonic vibrations through piezoelectric principles. Generator (12) may include a power source and control circuitry (16) that is configured to provide a power profile to transducer (26) that is particularly suited for the generation of ultrasonic vibrations through transducer assembly (12). Ultrasonic vibrations that are generated by transducer (26) are communicated along waveguide (148), which extends through shaft assembly (140) to reach ultrasonic blade (152). As can best be seen in FIG. 4, waveguide (148) is secured within shaft assembly (140) via a pin (147), which passes through a through-bore (145) in waveguide (148) and shaft assembly (140). Pin (147) is located at a position along the length of waveguide (148) corresponding to a node associated with resonant ultrasonic vibrations communicated through waveguide (148) (i.e., at an acoustic node). Through-bore (145) in waveguide (148) may be oriented orthogonal relative to the longitudinal axis of waveguide (148). Pin (147) is disposed in a bore (164) extending through an inner collar (162) of rotation member (160) to rotationally and longitudinally secure waveguide (148) relative to outer sheath (142). As noted above, when ultrasonic blade (152) is in an activated state (i.e., vibrating ultrasonically), ultrasonic blade (152) is operable to effectively cut through and seal tissue, particularly when the tissue is being clamped between clamp pad (156) and ultrasonic blade (152). It should be understood that waveguide (148) may be configured to amplify mechanical vibrations transmitted through waveguide (148). Furthermore, waveguide (148) may include features operable to control the gain of the longitudinal vibrations along waveguide (148) and/or features to tune waveguide (148) to the resonant frequency of the system.

In the present example, and as similarly described above with respect to surgical system (10), the distal end of ultrasonic blade (152) is located at a position corresponding to an anti-node associated with resonant ultrasonic vibrations communicated through waveguide (148), in order to tune the acoustic assembly to a preferred resonant frequency $f_o$ when the acoustic assembly is not loaded by tissue. When transducer (26) is energized, the distal end of ultrasonic blade (152) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through the waveguide to reach ultrasonic blade (152), thereby providing oscillation of ultrasonic blade (152) at the resonant ultrasonic frequency. Thus, when tissue is secured between ultrasonic blade (152) and clamp pad (156), the ultrasonic oscillation of ultrasonic blade (152) may simultaneously sever the tissue and denature the proteins in adjacent tissue cells, thereby providing a coagulative effect with relatively little thermal spread. In some versions, an electrical current may also be provided through ultrasonic blade (152) and/or clamp pad (156) to also seal the tissue.

As can be seen in FIGS. 3 and 4, waveguide (148) has a plurality of acoustic isolators (149) positioned along the longitudinal length of waveguide (148). Isolators (149) may provide structural support to waveguide (148); and/or acoustic isolation between waveguide (148) and other portions of shaft assembly (140). Isolators (149) generally have a circular or ovular cross-section and extend circumferentially around the diameter of waveguide (148). In some versions, isolators (149) comprise conventional o-rings. The inner diameter of each isolator (149) is generally sized slightly smaller than the outer diameter of waveguide (148) to create a slight interference fit, thus securing each isolator (149) to waveguide (148). In some examples, waveguide (148) may include annular, recessed channels that are configured to receive each isolator (149) to further aid in securing each isolator (149) along the longitudinal length of waveguide (148). In the present example, each isolator (149) is positioned at or near to an acoustic node along the longitudinal length of waveguide (148). Such positioning may reduce the vibrations transferred to isolators (149) (and to other components in contact with isolators (149)) via waveguide (148). Bore (145) is also positioned at a nodal position of waveguide (148). Because of this, the proximal most isolator (149) is positioned slightly distal to the nodal position of bore (145). As will be described in greater detail below, some versions of isolator (149) may be configured such that bore (145) and isolator (149) may occupy the same nodal position.

An operator may activate buttons (136) to selectively activate transducer (26) to thereby activate ultrasonic blade (152). In the present example, two buttons (136) are provided—one for activating ultrasonic blade (152) at a low power and another for activating ultrasonic blade (152) at a high power. However, it should be understood that any other suitable number of buttons and/or otherwise selectable power levels may be provided. For instance, a foot pedal may be provided to selectively activate transducer (26). Buttons (136) of the present example are positioned such that an operator may readily fully operate instrument (120) with a single hand. For instance, the operator may position their thumb about pistol grip (134), position their middle, ring, and/or little finger about trigger (138), and manipulate buttons (136) using their index finger. Of course, any other suitable techniques may be used to grip and operate instrument (120); and buttons (136) may be located at any other suitable positions.

The foregoing components and operabilities of instrument (120) are merely illustrative. Instrument (120) may be configured in numerous other ways as will be apparent to those of ordinary skill in the art in view of the teachings herein. By way of example only, at least part of instrument (120) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pat. No. 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S. Pat. No. 9,393,037, issued on Jul. 16, 2016; and/or U.S. Pub. No. 2014/0114334, now U.S. Pat. No. 9,095,367, issued on Aug. 4, 2015. Additional merely illustrative variations for instrument (120) will be described in greater detail below. It should be understood that the below described variations may be readily applied to instrument (120) described above and any of the instruments referred to in any of the references that are cited herein, among others.

B. Exemplary Ultrasonic Surgical Instrument for Open Surgical Procedures

Figure 5:
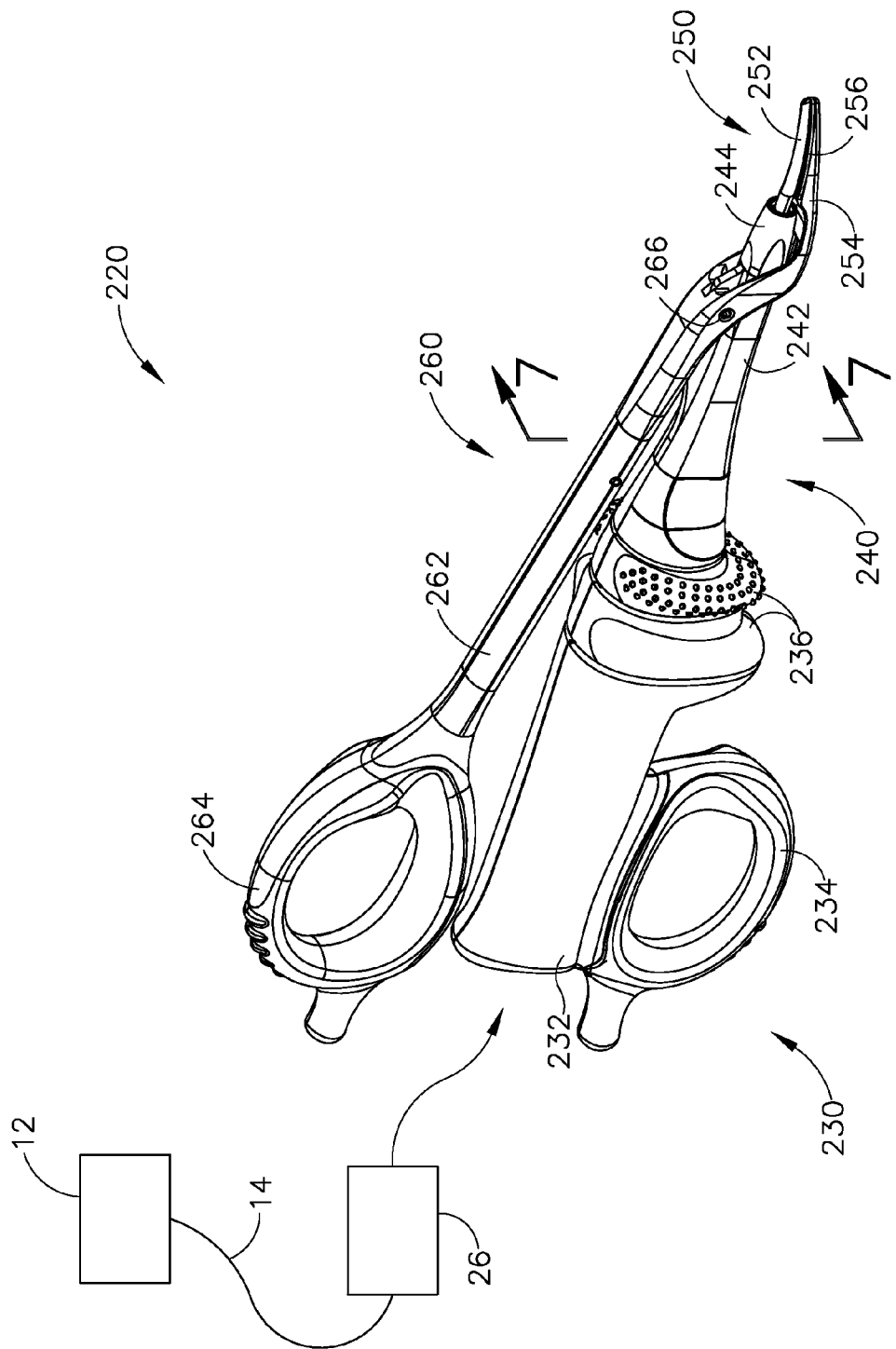
FIG. 5 depicts a perspective view of an exemplary alternative surgical instrument for use with the ultrasonic surgical system of FIG. 1.

FIG. 5 illustrates an exemplary ultrasonic surgical instrument (220) that is configured to be used in open surgical procedures. Instrument (220) of this example comprises a handle assembly (230), a shaft assembly (240), and an end effector (250). Handle assembly (230) comprises a body (232) including a finger grip ring (234) and a pair of buttons (236). Instrument (220) also includes a clamp arm assembly (260) that is pivotable toward and away from body (232). Clamp arm (260) includes a shank (262) with a thumb grip ring (264). Thumb grip ring (264) and finger grip ring (234) together provide a scissor grip type of configuration. It should be understood, however, that various other suitable configurations may be used, including but not limited to a pistol grip configuration.

Figure 6:
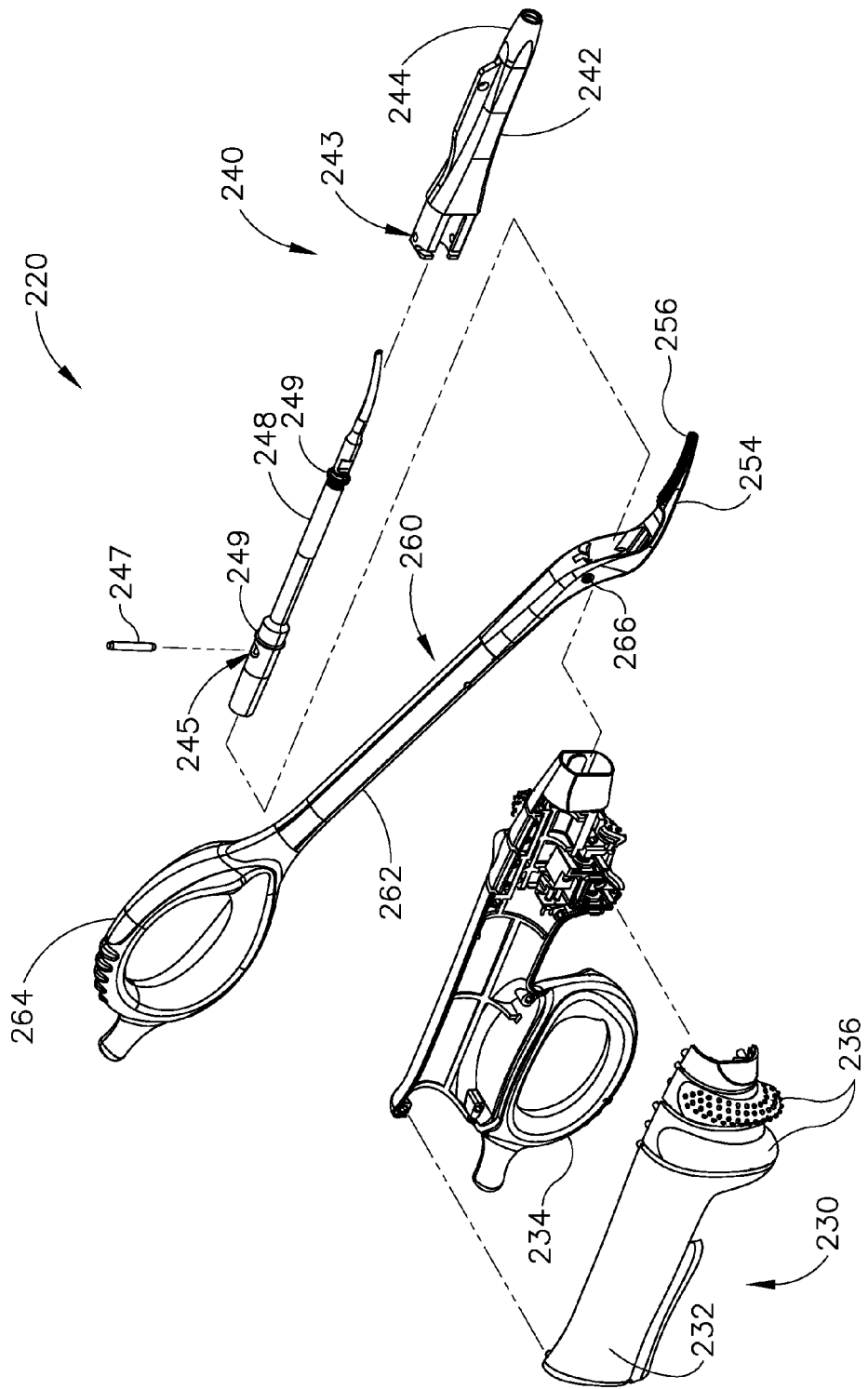
FIG. 6 depicts a partially exploded perspective view of the surgical instrument of FIG. 5.

Shaft assembly (240) comprises an outer sheath (242) extending distally from body (232). A cap (244) is secured to the distal end of sheath (242). As best seen in FIGS. 5-6, end effector (250) comprises an ultrasonic blade (252) and a clamp arm (254). Ultrasonic blade (252) extends distally from cap (244). Clamp arm (254) is an integral feature of clamp arm assembly (260). Clamp arm (254) includes a clamp pad (256) facing ultrasonic blade (252). Clamp arm assembly (260) is pivotally coupled with outer sheath (242) via a pin (266). Clamp arm (254) is positioned distal to pin (266); while shank (262) and thumb grip ring (264) are positioned proximal to pin (266). Thus, as seen in FIG. 5, clamp arm (254) is pivotable toward and away from ultrasonic blade (252) based on pivoting of thumb grip ring (264) toward and away from body (232) of handle assembly (230). It should therefore be understood that an operator may squeeze thumb grip ring (264) toward body (232) to thereby clamp tissue between clamp pad (256) and ultrasonic blade (252) to transect and/or seal the tissue. In some versions, one or more resilient members are used to bias clamp arm (254) to the open position such that clamp arm (254) is pivoted away from ultrasonic blade (252). By way of example only, such a resilient member may comprise a leaf spring, a torsion spring, and/or any other suitable kind of resilient member.

Referring to FIG. 5, ultrasonic transducer (26) of surgical system (10) may be received by body (232) of handle assembly (230). As similarly described above, transducer (26) is coupled with generator (12) via cable (14). Transducer (26) receives electrical power from generator (12) and converts that power into ultrasonic vibrations through piezoelectric principles. Generator (12) may include a power source and control module that is configured to provide a power profile to transducer (26) that is particularly suited for the generation of ultrasonic vibrations through transducer (26). Generator (12) may be constructed in accordance with at least some of the above teachings or any other construction as will be apparent to those of ordinary skill in the art in view of the teachings herein. Additionally, it should also be understood that at least some of the functionality of generator (12) may be integrated into handle assembly (230), and that handle assembly (230) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

Ultrasonic vibrations that are generated by transducer (26) are communicated along an acoustic waveguide (248), which extends through shaft assembly (240), to reach ultrasonic blade (252). As can best be seen in FIG. 7, waveguide (248) is secured within shaft assembly (240) via a pin (247), which passes through bore (245) of waveguide (248) and a bore (243) of outer sheath (242). Pin (247) is located at a position along the length of waveguide (248) corresponding to a node associated with resonant ultrasonic vibrations communicated through waveguide (248). As noted above, when ultrasonic blade (252) is in an activated state (i.e., vibrating ultrasonically), ultrasonic blade (252) is operable to effectively cut through and seal tissue, particularly when the tissue is being clamped between clamp pad (256) and ultrasonic blade (252). It should be understood that waveguide (248) may be configured to amplify mechanical vibrations transmitted through waveguide (248). Furthermore, waveguide (248) may include features operable to control the gain of the longitudinal vibrations along waveguide (248) and/or features to tune waveguide (248) to the resonant frequency of the system.

In the present example, the distal end of ultrasonic blade (252) is located at a position corresponding to an anti-node associated with resonant ultrasonic vibrations communicated through waveguide (248), in order to tune the acoustic assembly to a preferred resonant frequency fo when the acoustic assembly is not loaded by tissue. When transducer (26) is energized, the distal end of ultrasonic blade (252) is configured to move longitudinally in the range of, for example, approximately 10 to 500 microns peak-to-peak, and in some instances in the range of about 20 to about 200 microns at a predetermined vibratory frequency fo of, for example, 55.5 kHz. When transducer (26) of the present example is activated, these mechanical oscillations are transmitted through the waveguide to reach ultrasonic blade (252), thereby providing oscillation of ultrasonic blade (252) at the resonant ultrasonic frequency. Thus, when tissue is secured between ultrasonic blade (252) and clamp pad (256), the ultrasonic oscillation of ultrasonic blade (252) may simultaneously sever the tissue and denature the proteins in adjacent tissue cells, thereby providing a coagulative effect with relatively little thermal spread. In some versions, an electrical current may also be provided through ultrasonic blade (252) and/or clamp pad (256) to also seal the tissue.

Figure 7:
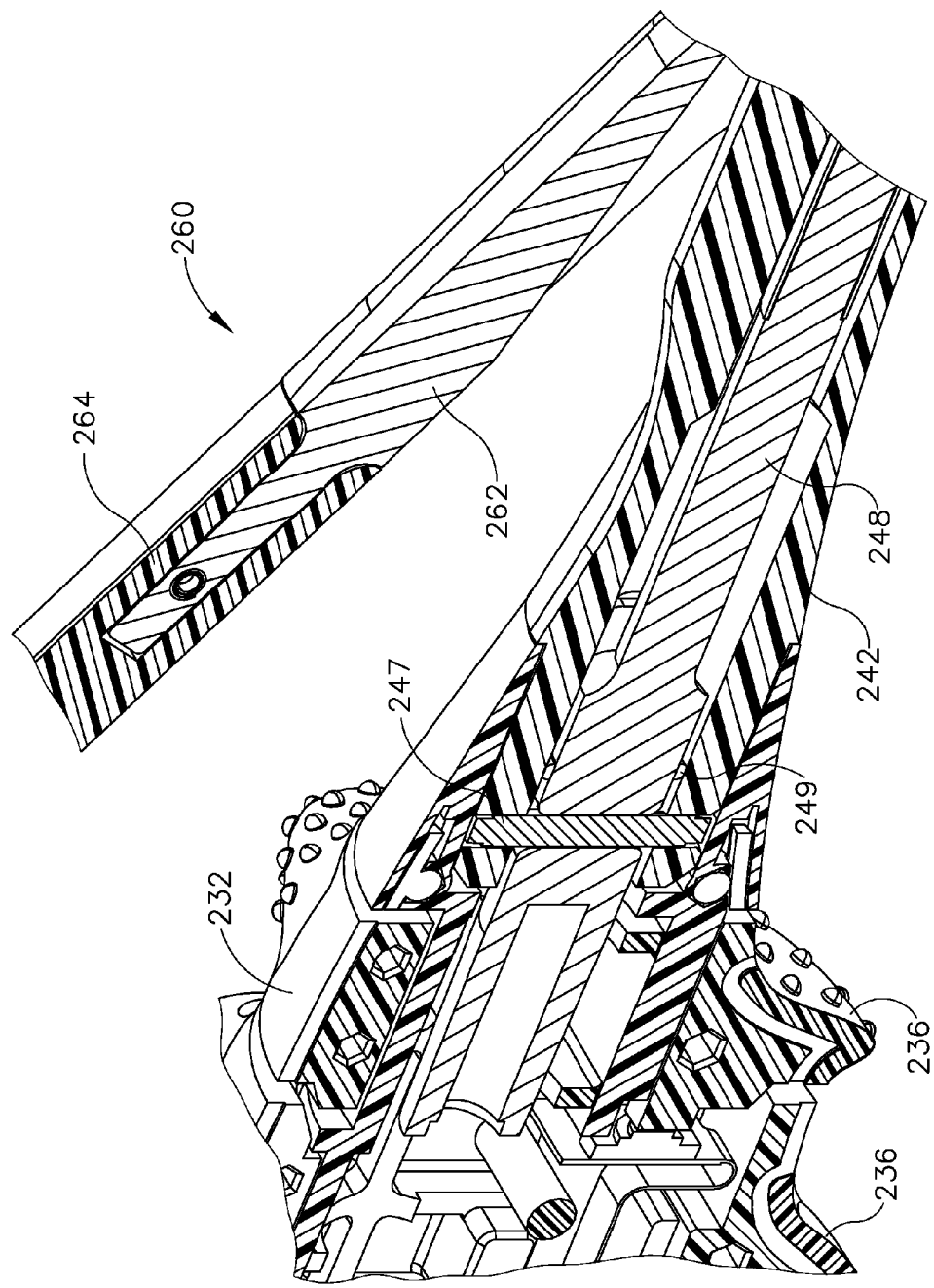
FIG. 7 depicts a perspective cross-sectional view of the surgical instrument of FIG. 5, with the cross-section taken along line 7-7 of FIG. 5.

As can be seen in FIGS. 6 and 7, waveguide (248) has a plurality of acoustic isolators (249) positioned along the longitudinal length of waveguide (248). Isolators (249) may provide structural support to waveguide (248); and/or acoustic isolation between waveguide (248) and other portions of shaft assembly (240). Isolators (249) generally have a circular or ovular cross-section and extend circumferentially around the diameter of waveguide (248). In some versions, isolators (249) comprise conventional o-rings. The inner diameter of each isolator (249) is generally sized slightly smaller than the outer diameter of waveguide (248) to create a slight interference fit, thus securing each isolator (249) to waveguide (248). In some examples, waveguide (248) may include annular, recessed channels that are configured to receive each isolator (249) to further aid in securing each isolator (249) along the longitudinal length of waveguide (248). In the present example, each isolator (249) is positioned at or near to an acoustic node along the longitudinal length of waveguide (248). Such positioning may reduce the vibrations transferred to isolators (249) (and to other components in contact with isolators (249)) via waveguide (248). Bore (245) of waveguide (248) is also positioned at a nodal position of waveguide (248). Because of this, the proximal most isolator (249) is positioned slightly distal to the nodal position of bore (245). As will be described in greater detail below, some versions of isolator (249) may be configured such that bore (245) and isolator (249) may occupy the same nodal position.

An operator may activate buttons (236) to selectively activate transducer (26) to thereby activate ultrasonic blade (252). In the present example, two buttons (236) are provided—one for activating ultrasonic blade (252) at a low power and another for activating ultrasonic blade (252) at a high power. However, it should be understood that any other suitable number of buttons and/or otherwise selectable power levels may be provided. For instance, a foot pedal may be provided to selectively activate transducer (26). Buttons (236) of the present example are positioned such that an operator may readily fully operate instrument (220) with a single hand. For instance, the operator may position their thumb within thumb grip ring (264), position their middle, ring, and/or little finger within finger grip ring (234), and manipulate buttons (236) using their index or middle finger. Of course, any other suitable techniques may be used to grip and operate instrument (220); and buttons (236) may be located at any other suitable positions.

The foregoing components and operabilities of instrument (220) are merely illustrative. Instrument (220) may be configured in numerous other ways as will be apparent to those of ordinary skill in the art in view of the teachings herein. By way of example only, at least part of instrument (220) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pat. No. 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S. Pat. No. 9,393,037, issued on Jul. 16, 2016; U.S. Pub. No. 2014/0114334, now U.S. Pat. No. 9,095,367, issued on Aug. 4, 2015; and/or U.S. patent application Ser. No. 14/031,665, published as U.S. Pub. No. 2015/0080925 on Mar. 19, 2015. Additional merely illustrative variations for instrument (220) will be described in greater detail below. It should be understood that the below described variations may be readily applied to instrument (220) described above and any of the instruments referred to in any of the references that are cited herein, among others.

C. Exemplary Ultrasonic Scalpel Instrument

Figure 8:
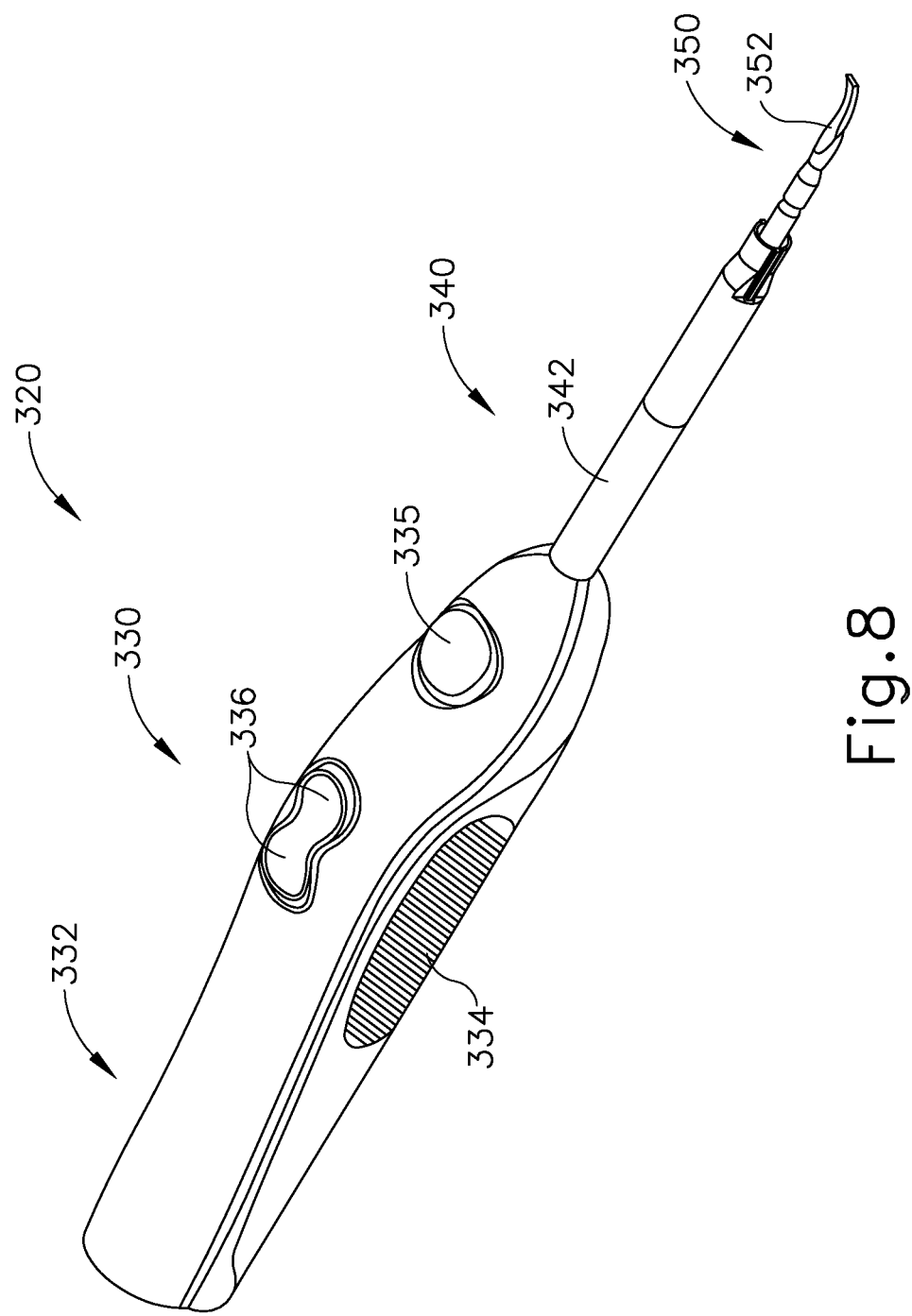
FIG. 8 depicts a perspective view of another exemplary surgical instrument for use with the ultrasonic surgical system of FIG. 1.

FIG. 8 illustrates an exemplary ultrasonic surgical instrument (320) that is configured to be used as a scalpel (e.g., in facial plastic surgery, etc.). Instrument (320) may be used in conjunction with ultrasonic surgical system (10) that includes ultrasonic transducer (26) coupled with ultrasonic generator (12) via cable (14). Instrument (320) of this example comprises a handle assembly (330), a shaft assembly (340), and an end effector (350). In some versions, handle assembly (330) may receive ultrasonic transducer (26) which may couple to a waveguide (348) in shaft assembly (340) by a threaded connection, though any other suitable type of coupling may be used. Handle assembly (330) comprises a tubular elongate body (332) including a grip portion (334) and a plurality of buttons (335, 336). Unlike handle assemblies (130, 230) discussed above, handle assembly (330) does not include a trigger or finger grip to actuate a clamp arm of end effector (350). Instead, a clamp arm is omitted and instrument is merely used as an ultrasonic scalpel for simultaneously slicing and cauterizing tissue. Thus, handle assembly (330) includes grip portion (334) which is configured to permit a user to grip handle assembly (330) from a variety of positions. By way of example only, handle assembly (330) may be shaped to be grasped and manipulated in a pencil-like arrangement. Handle assembly (330) of the present example comprises mating housing portions (337) and (338). While a multi-piece handle assembly (330) is illustrated, handle assembly (330) may alternatively comprise a single or unitary component. Handle assembly (330) may be constructed from a durable plastic, such as polycarbonate or a liquid crystal polymer. It is also contemplated that handle assembly (330) may alternatively be made from a variety of materials or combinations of materials, including but not limited to other plastics, ceramics, and/or metals, etc. In some versions, the proximal end of instrument (320) receives and is fitted with ultrasonic transducer (26) by insertion of ultrasonic transducer (26) into handle assembly (330). Instrument (220) may be attached to and removed from ultrasonic transducer (26) as a unit.

Figure 9:
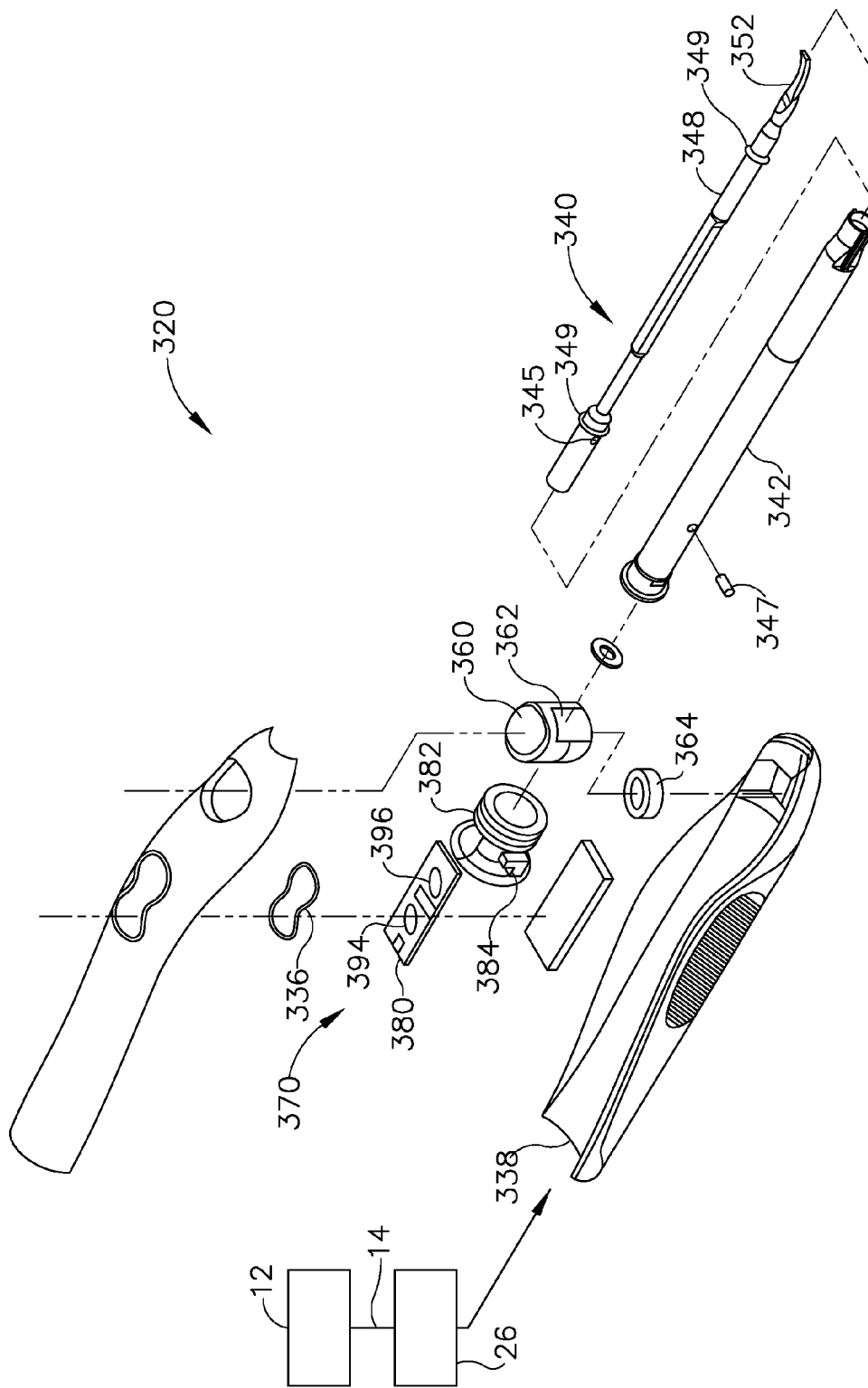
FIG. 9 depicts a perspective exploded view of the surgical instrument of FIG. 8.

As shown in FIG. 9, shaft assembly (340) comprises an outer sheath (342), and a waveguide (348) disposed within outer sheath (342). Waveguide (348), which is configured to transmit ultrasonic energy from transducer (26) to an ultrasonic blade (352), may be flexible, semi-flexible or rigid. Waveguide (348) may also be configured to amplify the mechanical vibrations transmitted through waveguide (348) to blade (352). Waveguide (348) may further include at least one bore (345) extending therethrough, substantially perpendicular to the longitudinal axis of waveguide (348). Bore (345) is located at a longitudinal position corresponding to a node associated with ultrasonic vibrations communicated along waveguide (348). Bore (345) is configured to receive a connector pin (347), discussed below, which connects ultrasonic waveguide (348) to outer sheath (342).

As described above, in contrast to end effectors (150, 250), end effector (350) omits clamp arm. Instead, end effector (350) merely consists of ultrasonic blade (352) which may be used for simultaneously slicing and cauterizing tissue. Blade (352) may be integral with ultrasonic waveguide (348) and formed as a single unit. In some versions, blade (352) may be connected to waveguide (348) by a threaded connection, a welded joint, and/or some other coupling feature(s). The distal end of blade (352) is disposed at or near a longitudinal position corresponding to an anti-node associated with ultrasonic vibrations communicated along waveguide (348) and blade (352) in order to tune the acoustic assembly to a preferred resonant frequency $f_o$ when the acoustic assembly is not loaded by tissue. When transducer (26) is energized, the distal end of blade (352) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (352) may also vibrate in the y-axis at about 1 to about 10 percent of the motion in the x-axis. Of course, movement of blade (352) may alternatively have any other suitable characteristics.

Waveguide (348) is positioned within outer sheath (342) and held in place via pin (347). Pin (347) may be made of any compatible metal, such as stainless steel or titanium or a durable plastic, such as polycarbonate or a liquid crystal polymer. Alternatively, any other suitable material or combination of materials may be used. In some versions, pin (347) is partially coated with an elastomeric material, such as silicon, etc., for the portion of pin (347) that extends through ultrasonic waveguide (348). Elastomeric material may provide insulation from the vibrating blade throughout the length of bore (345). In some settings, this may enable high efficiency operation whereby minimal overheating is generated and maximum ultrasonic output power is available at the distal end of blade (352) for cutting and coagulation, etc. Of course, such elastomeric material is merely optional.

As can be seen in FIG. 9, waveguide (348) has a plurality of acoustic isolators (349) positioned along the longitudinal length of waveguide (348). Isolators (349) may provide structural support to waveguide (348); and/or acoustic isolation between waveguide (348) and other portions of shaft assembly (340). Isolators (349) generally have a circular or ovular cross-section and extend circumferentially around the diameter of waveguide (348). The inner diameter of each isolator (349) is generally sized slightly smaller than the outer diameter of waveguide (348) to create a slight interference fit, thus securing each isolator (349) to waveguide (348). In some examples, waveguide (348) may include annular, recessed channels that are configured to receive each isolator (349) to further aid in securing each isolator (349) along the longitudinal length of waveguide (348). In the present example, each isolator (349) is positioned at or near to an acoustic node along the longitudinal length of waveguide (348). Such positioning may reduce the vibrations transferred to isolators (349) (and to other components in contact with isolators (349)) via waveguide (348). Bore (345) of waveguide (348) is also positioned at a nodal position of waveguide (348). Because of this, the proximal most isolator (349) is positioned just distal to the nodal position of bore (345). As will be described in greater detail below, some versions of isolator (349) may be configured such that bore (345) and isolator (349) may occupy the same nodal position.

Outer sheath (342) passes through an aperture (362) of release button (360). A spring (364) is positioned below button (335) and resiliently biases button (335) upwardly. The upward force imposed by spring (364) causes the perimeter of aperture (362) to firmly assert pressure against outer sheath (342), and thereby selectively prevents outer sheath (342), waveguide (348), and ultrasonic blade (352) from either rotating within handle assembly (330) or axially translating with respect to handle assembly (330). When the operator exerts a downward force on button (335), spring (364) is compressed and it no longer asserts a holding force on outer sheath (342). The operator may then axially translate outer sheath (342), waveguide (348), and blade (352) relative to handle assembly (330) and/or rotate outer sheath (342), waveguide (348), and blade (352) relative to handle assembly (330). Accordingly, it should be understood that the longitudinal and/or rotational position of blade (352) relative to handle assembly (330) may be selectively adjusted by the operator while depressing button (335), while still allowing blade (352) to vibrate ultrasonically at such selected positions, allowing blade (352) to be used in various surgical procedures at such selected positions. To initiate such ultrasonic action of blade (352), the operator may operate a footswitch (not shown), activate pair of buttons (336) as described below, activate a button on generator (12), or perform some other act on some component of system (10).

In the present example, body (332) of handle assembly (330) includes a proximal end, a distal end, and a cavity (338) extending longitudinally therein. Cavity (338) is configured to accept a switch assembly (370) and at least a portion of ultrasonic transducer assembly (26). In one some versions, the distal end of transducer (26) threadably attaches to the proximal end of waveguide (348), though any other suitable type of coupling may be used. Electrical contacts of transducer (26) also interface with switch assembly (370) to provide the operator with finger-activated controls on surgical instrument (320). Transducer (26) of the present example includes two conductive rings (not shown) which are securely disposed within the body of transducer (26). Merely exemplary transducers having such conductive rings are also described in U.S. Pat. No. 8,152,825, entitled "Medical Ultrasound System and Handpiece and Methods for Making and Tuning," issued Apr. 10, 2012, the disclosure of which is incorporated by reference herein. Switch assembly (370) of the present example comprises a pushbutton assembly (372), a circuit assembly (380), a switch housing (382), a first pin conductor (384), and a second pin conductor (not shown). Switch housing (382) is annular-shaped and is supported within handle assembly (330) by way of corresponding supporting mounts on switch housing (382) and body (332).

Pushbutton assembly (372) of the present example comprises pair of buttons (336). Circuit assembly (380) provides for the electro-mechanical interface between pair of buttons (336) and generator (12) via transducer (26). Circuit assembly (380) comprises two dome switches (394, 396) that are mechanically actuated by depressing each button of pair of buttons (336). Dome switches (394, 396) are electrical contact switches, that when depressed provide an electrical signal to generator (12). In particular, various components of circuit assembly (380) interface with transducer (26) via the ring conductors of transducer (26), which are in turn connected to conductors in cable (14) that connects to generator (12). In an exemplary operation, when the operator depresses one button of the pair of buttons (336), generator (12) may respond with a certain energy level, such as a maximum ("max") power setting. When the operator depresses another button of the pair of buttons (336), generator (12) may respond with a certain energy level, such as a minimum ("min") power setting, which conforms to accepted industry practice for pushbutton location and the corresponding power setting. Instrument (320) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability as will be apparent to those of ordinary skill in the art in view of the teachings herein.

In addition to or in lieu of being constructed in accordance with the above teachings, at least part of instrument (320) may be constructed and operable in accordance with at least some of the teachings of U.S. Pat. No. 5,322,055; U.S. Pat. No. 5,873,873; U.S. Pat. No. 5,980,510; U.S. Pat. No. 6,283,981; U.S. Pat. No. 6,309,400; U.S. Pat. No. 6,325,811; U.S. Pat. No. 6,423,082; U.S. Pat. No. 6,783,524; U.S. Pat. No. 8,057,498; U.S. Pat. No. 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2008/0234710; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S. Pat. No. 9,393,037, issued on Jul. 16, 2016; U.S. Pub. No. 2014/0114334, now U.S. Pat. No. 9,095,367, issued on Aug. 4, 2015; and/or U.S. Pat. App. No. 61/410,603. The disclosures of each of the foregoing patents, publications, and applications are incorporated by reference herein. Additional merely illustrative variations for instrument (320) will be apparent to those of ordinary skill in the art in view of the teachings herein. It should be understood that the below described variations may be readily applied to instrument (320) described above and any of the instruments referred to in any of the references that are cited herein, among others.

III. Exemplary Waveguide Variations

As noted above, surgical instruments (120, 220, 320) may include a shaft assembly (140, 240, 340) having at least a waveguide (148, 248, 348) and an outer sheath (142, 242, 342). In some circumstances it may be desirable to incorporate a plurality of acoustic isolators between waveguide (148, 248, 348) and outer sheath (142, 242, 342) to prevent the transfer of vibrations between waveguide (148, 248, 348) and outer sheath (142, 242, 342). Isolators may be placed at or near nodal positions associated with resonant ultrasonic vibrations communicated through waveguide (148, 248, 348). Positioning isolators at such a position along the length of waveguide (148, 248, 348) provides a position relatively free from acoustic vibration. However, in some circumstances it may be desirable to place other components besides an isolator at a given nodal position. Accordingly, various alternative waveguides are contemplated that permit mounting of isolators and other components at a single nodal position.

Figure 10:
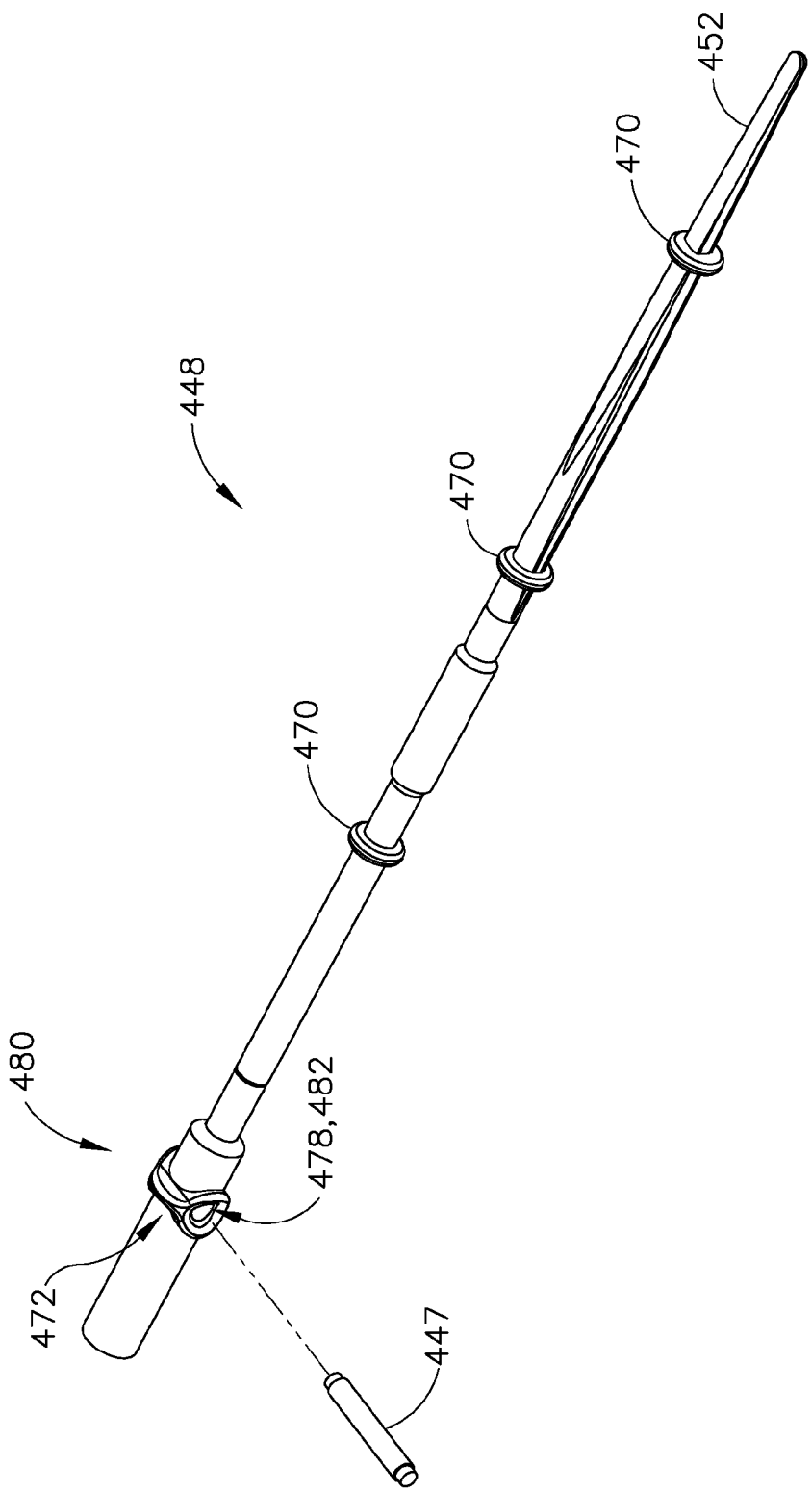
FIG. 10 depicts a perspective view of an exemplary waveguide for use with one or more of the surgical instruments of FIGS. 2, 5, and 8.
Figure 11:
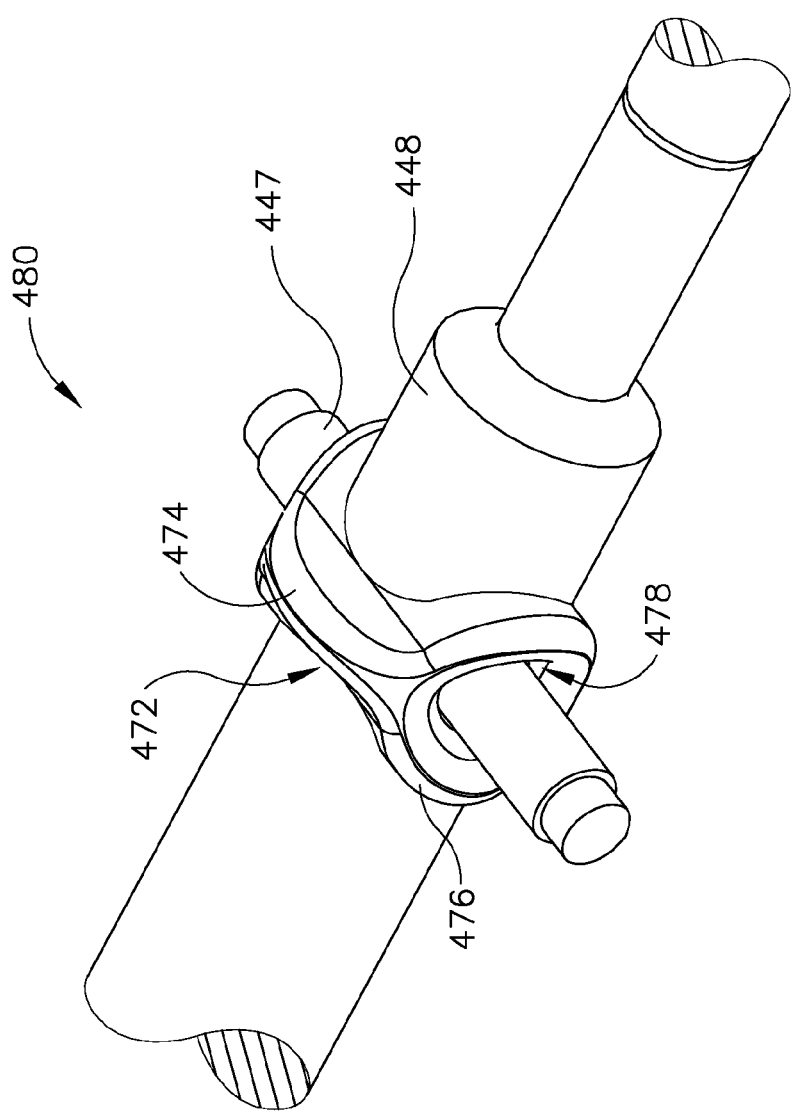
FIG. 11 depicts a detailed perspective view of a pin junction of the waveguide of FIG. 10.
Figure 12:
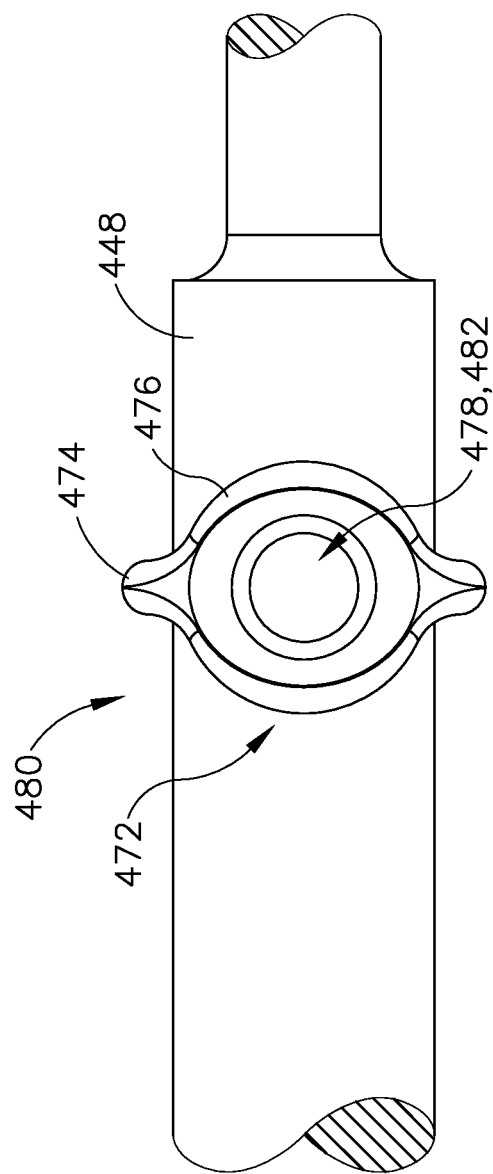
FIG. 12 depicts a detailed top plan view of the pin junction of FIG. 11, with a pin removed.
Figure 13:
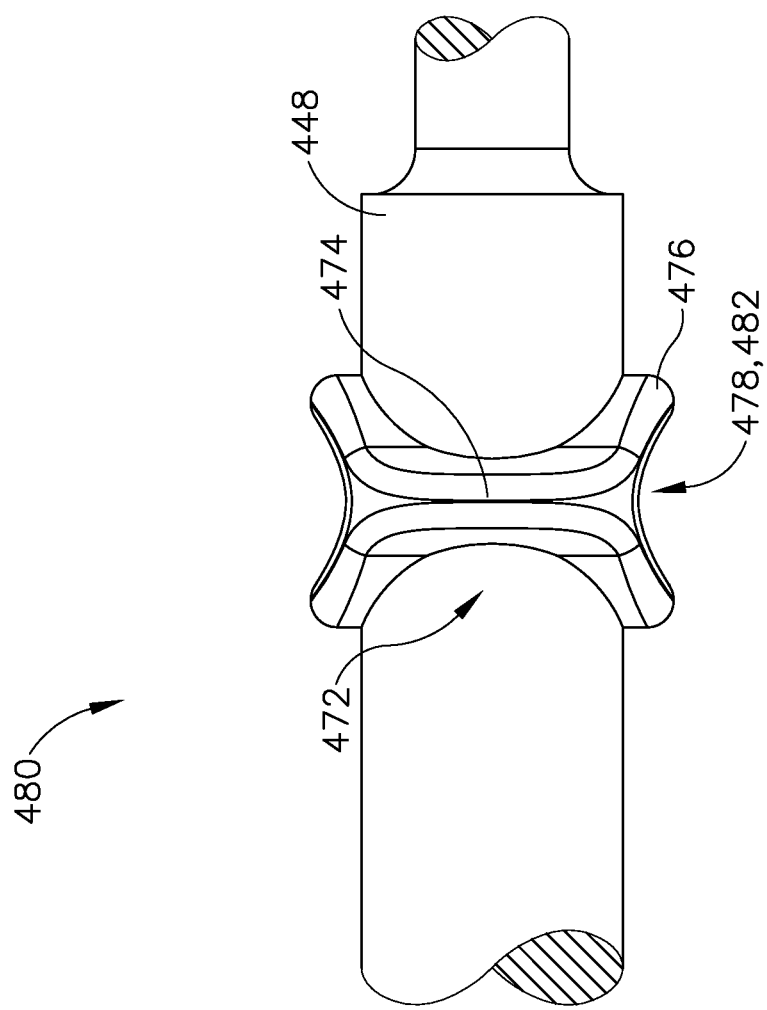
FIG. 13 depicts a detailed side elevational view of the pin junction of FIG. 11, with the pin removed.
Figure 14:
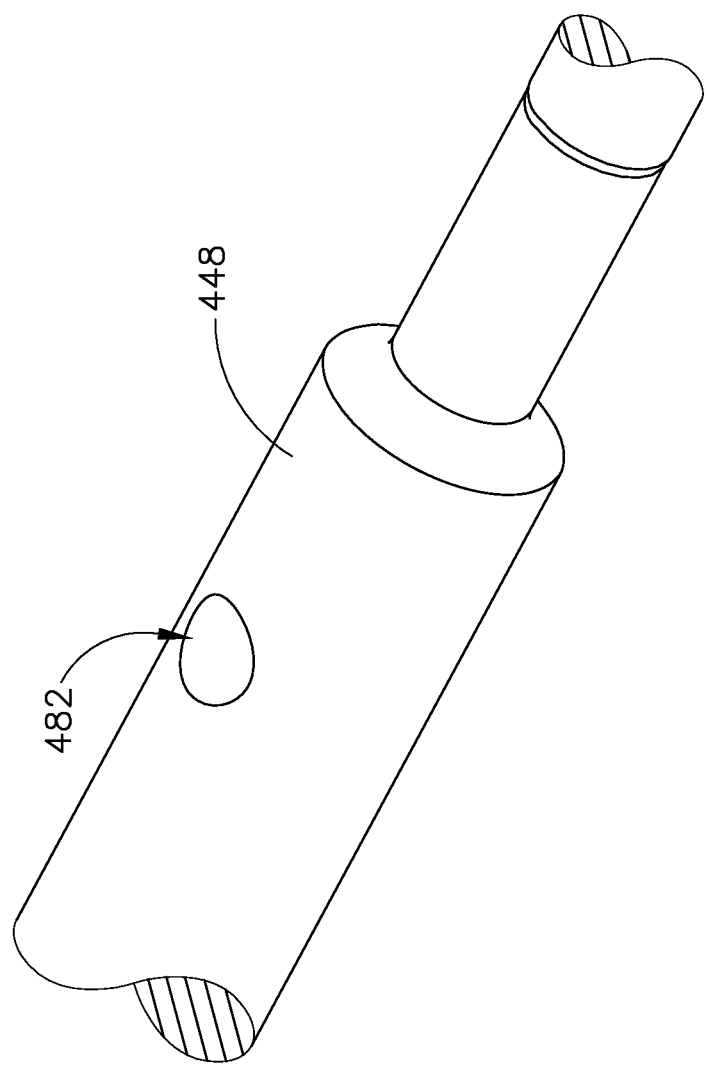
FIG. 14 depicts a detailed perspective view of the pin junction of FIG. 11, with an isolator removed.

FIG. 10 shows an exemplary alternative acoustic waveguide (448) for use with surgical instruments (120, 220, 320). As noted above with respect to waveguides (148, 248, 348), waveguide (448) may be flexible, semi-flexible, rigid, or have any other suitable properties. Similarly, ultrasonic transducer (26) may be integrally coupled with a blade (452) via waveguide (448) such that blade (452) may vibrate at ultrasonic frequencies when transducer (26) is activated. In some versions, waveguide (448) may amplify the mechanical vibrations transmitted through waveguide (448) to blade (452). Waveguide (448) may further have features to control the gain of the longitudinal vibrations along waveguide (448) and/or features to tune waveguide (448) to the resonant frequency of system (10). For instance, waveguide (448) may have any suitable cross-sectional dimensions/configurations, such as a substantially uniform cross-section, be tapered at various sections, be tapered along its entire length, or have any other suitable configuration. Waveguide (448) and blade (452) may be fabricated from a solid core shaft constructed out of a material or combination of materials that propagates ultrasonic energy efficiently, such as titanium alloy (i.e., Ti-6Al-4V), aluminum alloys, sapphire crystal, stainless steel, or any other acoustically compatible material or combination of materials.

In the present example, waveguide (448) is shown as being equipped with a plurality of isolators (470, 472) positioned at nodes along the longitudinal length of waveguide (448). As described above, positioning isolators (470, 472) at nodal positions provides a relatively vibration free surface for each isolator (470, 472) to be positioned at. Thus, vibration transfer from waveguide (448) to other components of surgical instrument (120, 220, 320) via isolators (470, 472) will be minimized. Isolators (470, 472) are generally comprised of a relatively soft, elastomeric material such as rubber, silicone, or the like. Such a material may act to acoustically insulate waveguide (448) from other components of surgical instrument (120, 220, 320) where (470, 472) isolators make contact.

Isolators (470) positioned distally on waveguide (448) are shown as being generally round in shape, similar to an o-ring. Thus, isolators (470) extend outwardly from waveguide (448) and provide vibratory isolation around the perimeter of waveguide (448). Isolators (470) may be secured to waveguide (448) by any suitable means. For instance, in some examples, waveguide (448) may include annular, recessed channels for isolators (470). In such an example, the inner diameter of isolators (470) may be sized slightly smaller than the outer diameter of waveguide (448) such that isolators (470) are resiliently biased to fit into a corresponding annular channel. In other examples, isolators (470) may be secured to waveguide (448) by adhesive bonding or may simply be overmolded to waveguide (448). Of course, any other suitable means of securing isolators (470) to waveguide (448) may be used as will be apparent to those of ordinary skill in the art in view of the teachings herein.

As can best be seen in FIG. 11-14, waveguide (448) includes a proximal pin junction (480). Pin junction comprises a pin (447), a bore (482), and an isolator (472). As similarly discussed above with respect to waveguides (148, 248, 348), pin (447) is insertable into waveguide (448) through bore (482) to provide a means to longitudinally anchor waveguide (448) to surgical instrument (120, 220, 320). In the present example pin (447) is insertable into waveguide (448) orthogonally relative to the longitudinal axis of waveguide (448), although such an orientation may be of any suitable angle relative to the longitudinal axis of waveguide (448). It should be understood that because pin (447) contacts both waveguide (448) and other portions of surgical instrument (120, 220, 320), pin (447) may be placed at a nodal position to prevent or minimize transfer of vibrations from waveguide (448) to surgical instrument (120, 220, 320).

Isolator (472) is positioned at the same nodal position as pin (447) to similarly reduce or eliminate the transfer of vibrations from waveguide (448) to surgical instrument (120, 220, 320). In particular, isolator (472) is shaped to surround waveguide (448) at a consistent outer diameter such that isolator (472) may uniformly contact a mating component of surgical instrument (120, 220, 320). Yet, unlike isolators (470) discussed above, isolator (472) is shaped to accommodate pin (447) through the center of isolator (472) while still maintaining insulating properties around the perimeter of waveguide (448). In particular, isolator (472) comprises a laterally extending portion (474) and a rounded portion (476). Laterally extending portion (474) is similar in shape to isolators (470) discussed above, in that laterally extending portion (474) is rounded in shape similar to an o-ring. Additionally, laterally extending portion (474) extends along a plane that is perpendicular to the longitudinal axis of waveguide (448). Laterally extending portion (474) is coaxially positioned about the longitudinal axis of waveguide (448). Pin (447) is oriented generally parallel to laterally extending portion (474) and extends along the same plane as laterally extending portion (474). Thus, the longitudinal axis of pin (447) is perpendicular to the longitudinal axis of waveguide (448).

Rounded portion (476) extends along a plane that is generally parallel to the longitudinal axis of waveguide (448) and that is generally perpendicular to the longitudinal axis of pin (447). Further, rounded portion (476) extends circumferentially and coaxially about the longitudinal axis of pin (447). Rounded portion (476) extends outwardly from waveguide (448) the same distance as with laterally extending portion (474). Thus, isolator (472) provides a consistent outer diameter about the circumference of waveguide (448). However, rounded portion curves around bore (482) to define an opening (478) in isolator (472) that has a diameter greater than or equal to the diameter of bore (482).

In some examples, isolator (472) may be secured to waveguide (448) by overmolding isolator (472) directly to waveguide (448). For such examples, bore (482) may be sealed off to prevent flashing (from the overmolding procedure) from entering bore (482) or interfering with pin (447). Otherwise, the presence of flash in bore (482) may cause a buildup of excessive heat. Additionally, bore (482) may include a chamfered edge (e.g., at each end of bore (482)), which may be used in the process of sealing bore (482) to avoid penetration of flash. For instance, in some examples, the overmolding process may include an overmolding tool configured to seal and/or shunt off bore (482) during the overmolding process. Where such a tool is used, a chamfered edge of bore (482) may provide a contact surface for the overmolding tool to mate with, thereby providing a tight seal between the overmolding tool and waveguide (448). A chamfer may also facilitate insertion of pin (447) through opening (478). In other examples, isolator (472) may be produced separately and secured to waveguide (448) by adhesive bonding. Of course, any other suitable procedure to make isolator (472) and/or secure isolator (472) to waveguide (448) may be used as will be apparent to those of ordinary skill in the art in view of the teachings herein.

Figure 15:
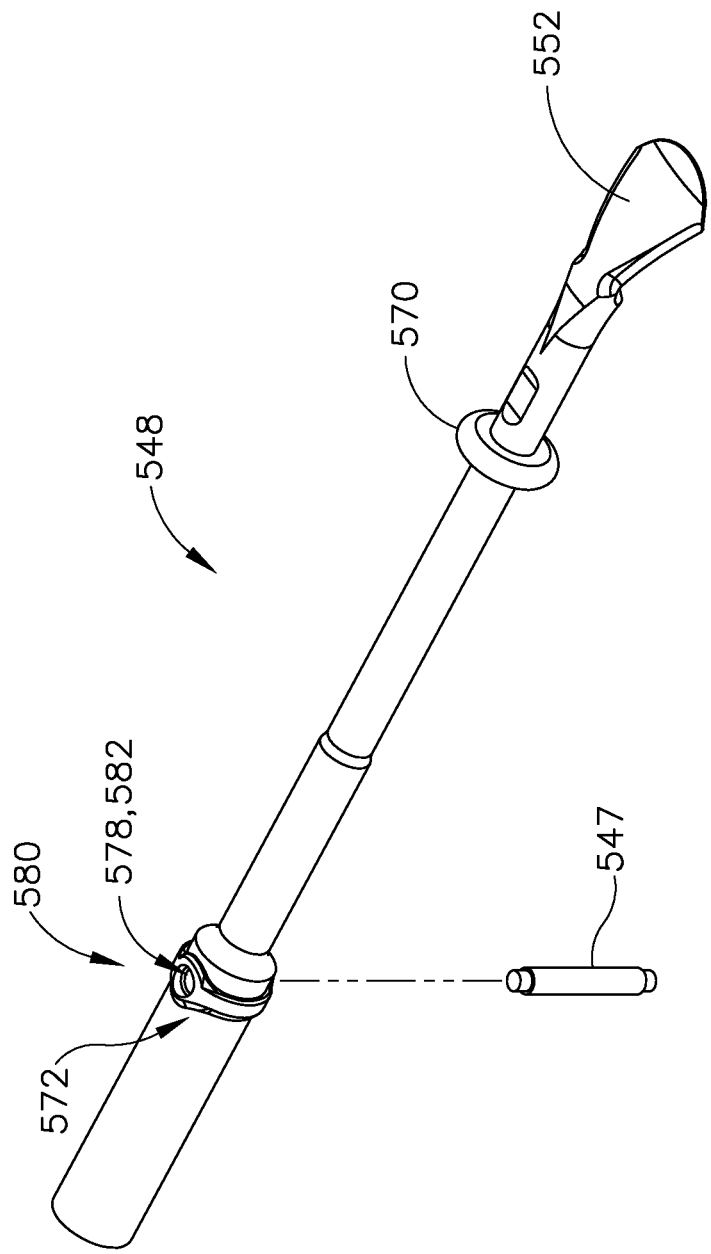
FIG. 15 depicts a perspective view of another exemplary waveguide for use with one or more of the surgical instruments of FIGS. 2, 5, and 8.
Figure 16:
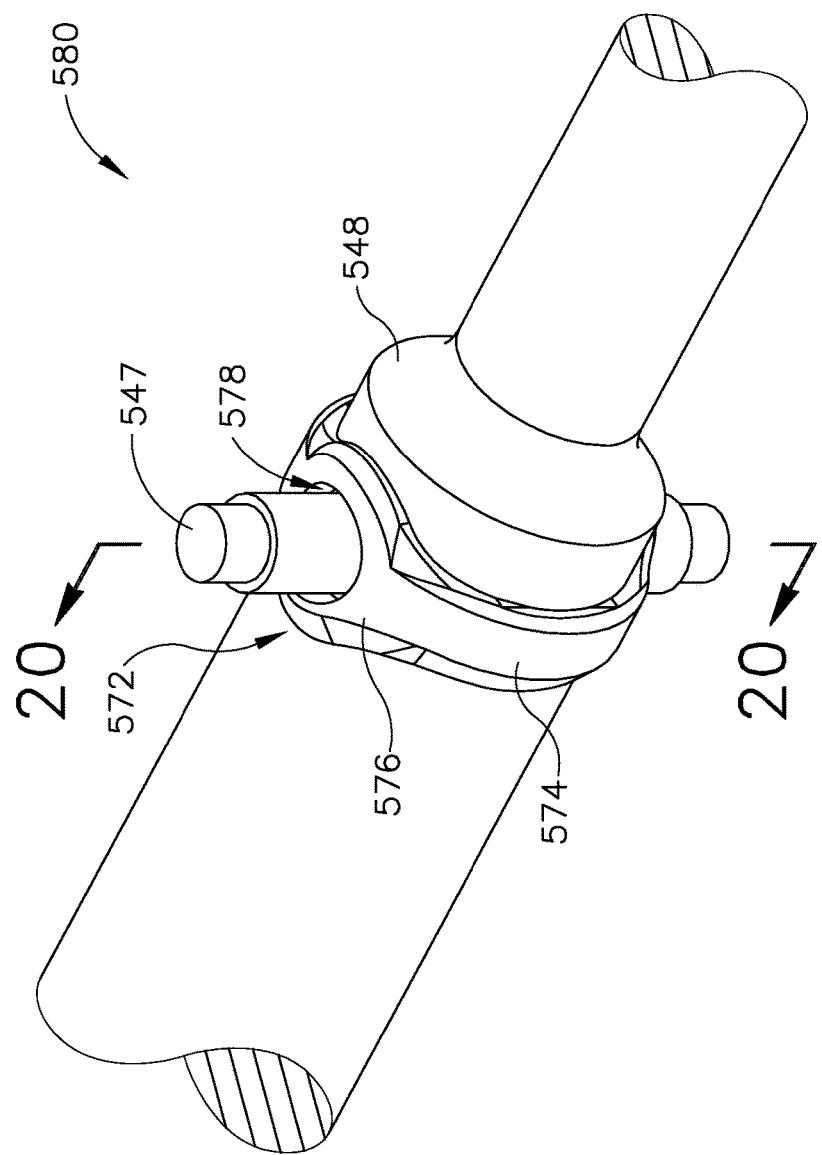
FIG. 16 depicts a detailed perspective view of a pin junction of the waveguide of FIG. 15.
Figure 17:
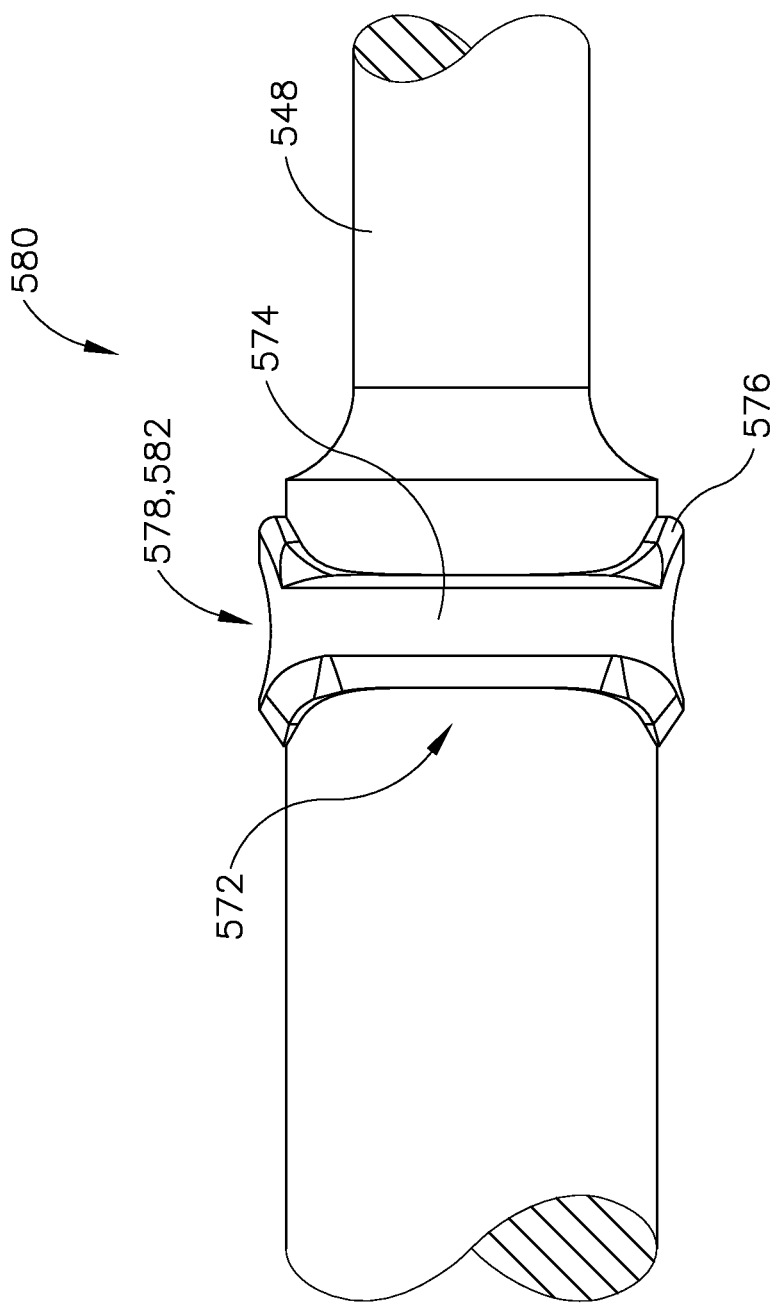
FIG. 17 depicts a detailed side elevational view of the pin junction of FIG. 16, with a pin removed.
Figure 18:
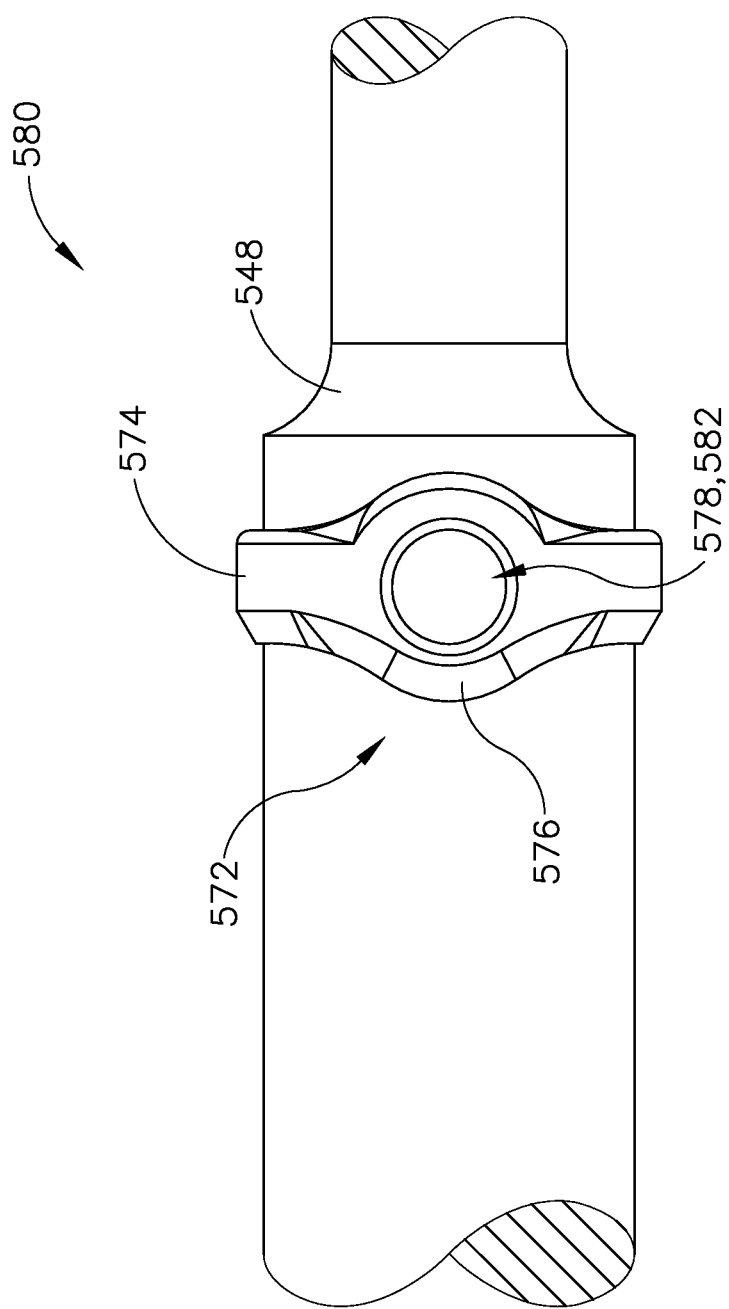
FIG. 18 depicts a detailed top plan view of the pin junction of FIG. 16, with the pin removed.

FIG. 15 shows another exemplary alternative acoustic waveguide (548) for use with surgical instruments (120, 220, 320), although waveguide (548) may be particularly suited for surgical instrument (320). Waveguide (548) of the present example is configured to operate at a continuous duty cycle and still meet International Electrotechnical Commission (IEC) heat standards, although the inventors contemplate that some versions of waveguide (548) may not necessarily meet such standards. As noted above with respect to waveguides (148, 248, 348, 448), waveguide (548) may be flexible, semi-flexible, rigid, or have any other suitable properties. Similarly, ultrasonic transducer (26) may be integrally coupled with a blade (552) via waveguide (548) such that blade (552) may vibrate at ultrasonic frequencies when transducer (26) is activated. Blade (552) in the present example is shaped to scrape tissue from bone in addition to slicing and/or cutting tissue. In some versions, waveguide (548) may amplify the mechanical vibrations transmitted through waveguide (548) to blade (552). Waveguide (548) may further have features to control the gain of the longitudinal vibrations along waveguide (548) and/or features to tune waveguide (548) to the resonant frequency of system (10). For instance, waveguide (548) may have any suitable cross-sectional dimensions/configurations, such as a substantially uniform cross-section, be tapered at various sections, be tapered along its entire length, or have any other suitable configuration. Waveguide (548) and blade (552) may be fabricated from a solid core shaft constructed out of a material or combination of materials that propagates ultrasonic energy efficiently, such as titanium alloy (i.e., Ti-6Al-4V), aluminum alloys, sapphire crystal, stainless steel, or any other acoustically compatible material or combination of materials.

In the present example, waveguide (548) is shown as being equipped with two isolators (570, 572) positioned at nodes along the longitudinal length of waveguide (548). As described above, positioning isolators (570, 572) at nodal positions provides a relatively vibration free surface for each isolator (570, 572) to be positioned at. Thus, vibration transfer from waveguide (548) to other components of surgical instrument (120, 220, 320) via isolators (570, 572) will be minimized. Isolators (520, 572) are generally comprised of a relatively soft, elastomeric material such as rubber, silicone, or the like. Such a material may act to acoustically insulate waveguide (548) from other components of surgical instrument (120, 220, 320) where isolators (570, 572) make contact.

Isolator (570) that is positioned distally on waveguide (548) is shown as being generally round in shape, similar to an o-ring. Thus, isolator (570) extends outwardly from waveguide (548) and provides vibratory isolation around the perimeter of waveguide (548). Isolator (570) may be secured to waveguide (548) by any suitable means. For instance, in some examples, waveguide (548) may include recessed, annular channels for isolator (570). In such examples, the inner diameter of isolator (570) may be sized slightly smaller than the outer diameter of waveguide (548) such that isolator (570) is resiliently biased to fit into a corresponding annular channel. In other examples, isolator (570) may be secured to waveguide (548) by adhesive bonding or may simply be overmolded to waveguide (548). Of course, any other suitable means of securing isolators (570) to waveguide (548) may be used as will be apparent to those of ordinary skill in the art in view of the teachings herein.

Figure 19:
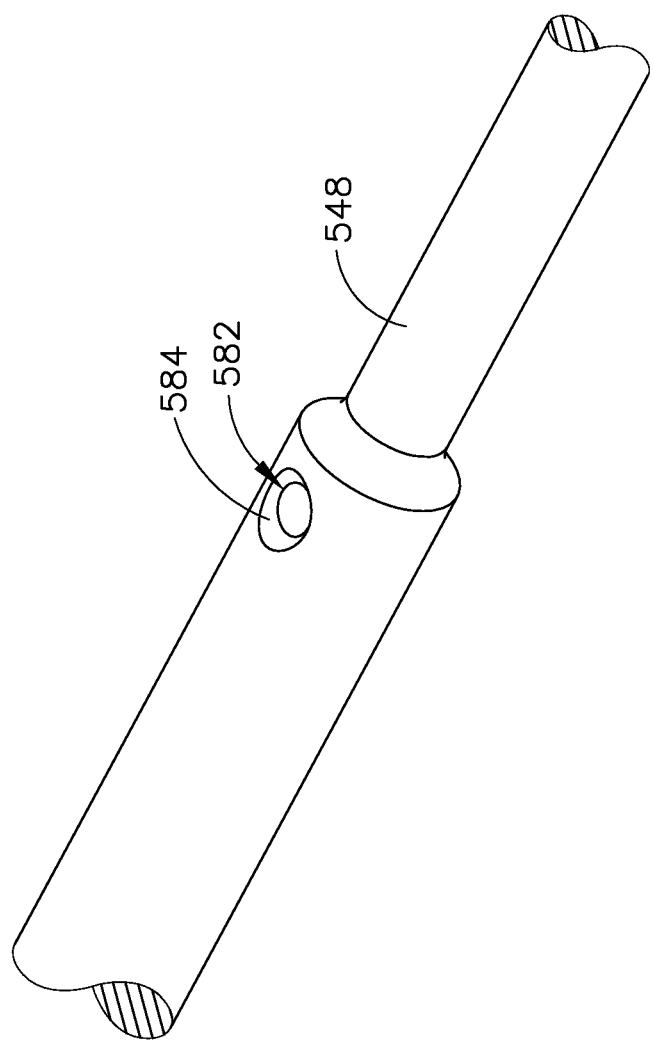
FIG. 19 depicts a detailed perspective view of the pin junction of FIG. 16, with an isolator removed.
Figure 20:
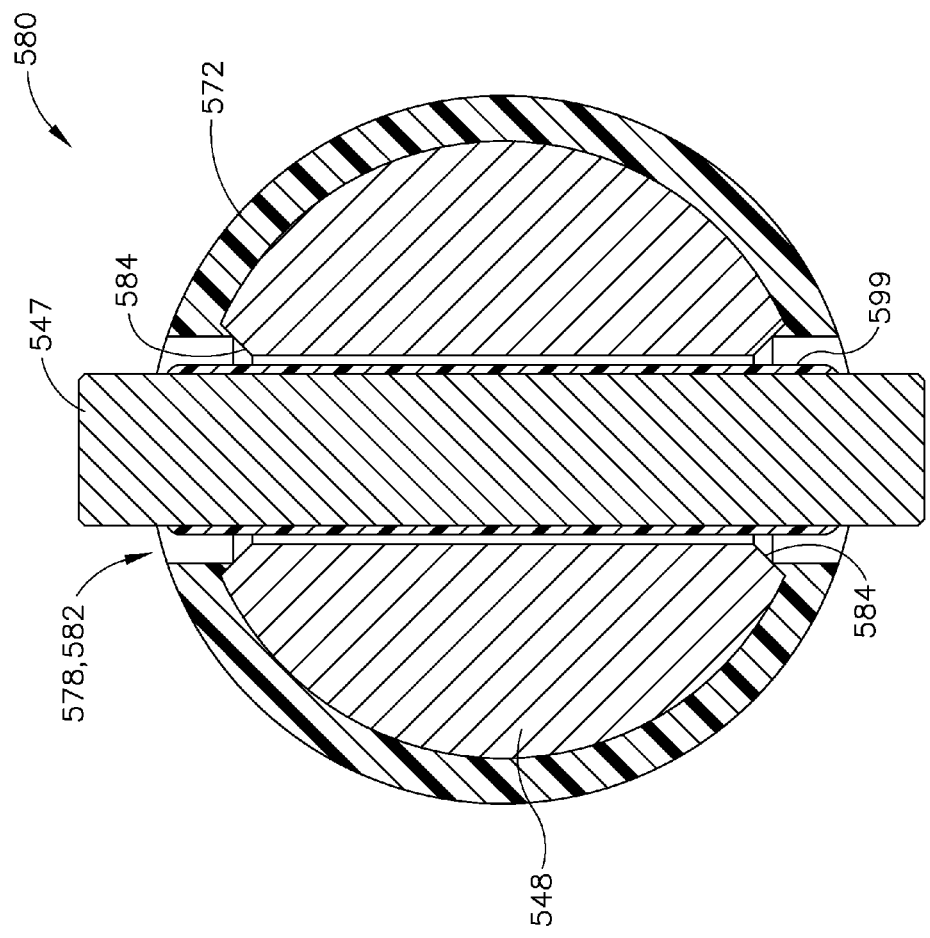
FIG. 20 depicts a front cross-sectional view of the pin junction of FIG. 16, with the cross-section taken along line 20-20 of FIG. 16.

As can best be seen in FIG. 16-20, waveguide (548) includes a proximal pin junction (580). Pin junction comprises a pin (547), a bore (582), and an isolator (572). As similarly discussed above with respect to waveguides (148, 248, 348), pin (547) is insertable into waveguide (548) through bore (582) to provide a means to longitudinally anchor waveguide (548) to surgical instrument (120, 220, 320). In the present example pin (547) is insertable into waveguide (548) orthogonally relative to the longitudinal axis of waveguide (548), although such an orientation may be of any suitable angle relative to the longitudinal axis of waveguide (548). It should be understood that because pin (547) contacts both waveguide (548) and other portions of surgical instrument (120, 220, 320), pin (547) may be placed at a nodal position to prevent or minimize transfer of vibrations from waveguide (548) to surgical instrument (120, 220, 320). In some examples, at least a portion of pin (547) may be coated with a layer of silicone (599) (FIG. 20) and/or some other material(s) to further reduce vibration transfer, although such a coating is entirely optional. By way of example only, and as shown in FIG. 20, some versions may include a layer of silicone (599) along only the portion of pin (547) that is within bore (582). Some other versions may include a layer of silicone (599) along the entire length of pin (547). In addition, some versions may further include silicone (599) across each end of pin (547). Various suitable ways in which pin (547) may include a full or partial coating of silicone (599) will be apparent to those of ordinary skill in the art in view of the teachings herein. It should also be understood that bore (582) may include a full or partial coating of silicone (599) and/or some other material(s) to further reduce vibration transfer, in addition to or as an alternative to pin (547) including a coating of silicone (599) and/or some other material(s) to further reduce vibration transfer.

Isolator (572) is positioned at the same nodal position as pin (547) to similarly reduce or eliminate the transfer of vibrations from waveguide (548) to surgical instrument (120, 220, 320). In particular, isolator (572) is shaped to surround waveguide (548) at a consistent outer diameter such that isolator (572) may uniformly contact a mating component of surgical instrument (120, 220, 320). Yet, unlike isolator (570) discussed above, isolator (572) is shaped to accommodate pin (547) through the center of isolator (572) while still maintaining insulating properties around the perimeter of waveguide (548). In particular, isolator (572) comprises a laterally extending portion (574) and a circular portion (576). Laterally extending portion (574) is similar in shape to isolator (570) discussed above, in that laterally extending portion (574) is rounded in shape similar to an o-ring. Additionally, laterally extending portion (574) extends along a plane that is perpendicular to the longitudinal axis of waveguide (548). Laterally extending portion (574) is coaxially positioned about the longitudinal axis of waveguide (548). Pin (547) is oriented generally parallel to laterally extending portion (574) and extends along the same plane as laterally extending portion (574). Thus, the longitudinal axis of pin (547) is perpendicular to the longitudinal axis of waveguide (548).

Rounded portion (576) extends along a plane that is generally parallel to the longitudinal axis of waveguide (548) and that is generally perpendicular to the longitudinal axis of pin (547). Further, rounded portion (576) extends circumferentially about the longitudinal axis of pin (547). Rounded portion (576) extends outwardly from waveguide (548) the same distance as with laterally extending portion (574). Thus, isolator (572) provides a consistent outer diameter about the circumference of waveguide (548). However, rounded portion curves around bore (582) to define an opening (578) in isolator (572) that is greater than or equal to the diameter of bore (582).

In some examples, isolator (572) may be secured to waveguide (548) by overmolding isolator (572) directly to waveguide (548). For such examples, bore (582) may be sealed off to prevent flashing from the overmolding procedure from entering bore (582) or interfering with pin (547). As can be seen in FIG. 19, bore (582) includes a chamfered edge (584) which may be used for sealing bore (584). It should be understood that each end of bore (582) may include a respective chamfered edge (584). In some examples, the overmolding process may include an overmolding tool configured to seal and/or shunt off bore (582) during the overmolding process. Where such a tool is used, chamfered edge (584) may provide a contact surface for the overmolding tool to mate with, thereby providing a tight seal between the overmolding tool and waveguide (548). Chamfered edge (584) may also facilitate insertion of pin (547) through opening (578) in isolator (572) and bore (582) of waveguide (548). It should be understood that chamfered edge (584) is entirely optional and may be omitted from other examples. In other examples, isolator (572) may be produced separately and secured to waveguide (548) by adhesive bonding. Of course, any other suitable procedure to make isolator (572) and/or secure isolator (572) to waveguide (548) may be used as will be apparent to those of ordinary skill in the art in view of the teachings herein.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) an ultrasonic transducer;
   (b) an acoustic waveguide in acoustic communication with the ultrasonic transducer, wherein the acoustic waveguide defines a longitudinal axis, wherein the acoustic waveguide comprises:
      (i) a bore extending transversely through the waveguide, wherein the bore defines a bore opening diameter,
      (ii) an anchor pin, wherein the anchor pin is insertable through the bore and is operable to secure the acoustic waveguide relative to the ultrasonic instrument, and
      (iii) an acoustic isolator, wherein the acoustic isolator is disposed about the acoustic waveguide and is operable to acoustically isolate the acoustic waveguide, wherein the acoustic isolator comprises a first opening extending through the isolator, wherein the opening is configured to receive the anchor pin, wherein the first opening defines a first opening diameter, wherein the first opening diameter is greater than the bore opening diameter; and
   (c) an ultrasonic blade in acoustic communication with the acoustic waveguide such that the ultrasonic transducer is operable to drive the ultrasonic blade to vibrate ultrasonically via the acoustic waveguide.

2. The ultrasonic instrument of claim 1, wherein the acoustic isolator comprises an elastomeric material.

3. The ultrasonic instrument of claim 1, wherein the acoustic isolator comprises silicone.

4. The ultrasonic instrument of claim 1, wherein the acoustic isolator is positioned at an acoustic node along the longitudinal length of the acoustic waveguide.

5. The ultrasonic instrument of claim 4, wherein the acoustic isolator, the bore, and the pin are all disposed at the same node along the longitudinal axis of the acoustic waveguide.

6. The ultrasonic instrument of claim 1, wherein the waveguide further comprises an o-ring positioned at a nodal position along the longitudinal axis of the acoustic waveguide, wherein the o-ring is positioned distally of the acoustic isolator.

7. The ultrasonic instrument of claim 6, wherein the o-ring is configured to acoustically isolate the acoustic waveguide.

8. The ultrasonic instrument of claim 1, wherein the anchor pin of the acoustic waveguide is oriented orthogonally relative to the longitudinal axis of the acoustic waveguide.

9. The ultrasonic instrument of claim 1, wherein the bore of the acoustic waveguide is chamfered, wherein the acoustic isolator abuts a portion of the chamfer.

10. The ultrasonic instrument of claim 1, wherein the first opening of the acoustic isolator is aligned over the bore of the acoustic waveguide.

11. The ultrasonic instrument of claim 1, wherein the acoustic isolator further comprises a second opening.

12. The ultrasonic instrument of claim 11, wherein the anchor pin is insertable into the first opening of the acoustic isolator and the acoustic waveguide extends through the second opening of the acoustic isolator.

13. The ultrasonic instrument of claim 11, wherein the second opening is perpendicular to the first opening.

14. The ultrasonic instrument of claim 1, wherein the acoustic isolator extends outwardly from the waveguide such that the acoustic isolator has a substantially uniform thickness.

15. An ultrasonic instrument comprising:
   (a) an ultrasonic transducer, wherein the ultrasonic transducer is operable to convert electrical power into ultrasonic vibrations;
   (b) an acoustic waveguide in acoustic communication with the ultrasonic transducer, wherein the acoustic waveguide defines a first longitudinal axis, wherein the acoustic waveguide comprises:
      (i) a bore extending through the acoustic waveguide, wherein the bore defines a second axis,
      (ii) an anchor pin configured to be received within the bore, and
      (iii) an acoustic isolator, wherein the acoustic isolator surrounds a portion of the acoustic waveguide, wherein the acoustic isolator comprises an opening extending along the first longitudinal axis from a first edge of the acoustic isolator to a second edge of the acoustic isolator, wherein the first edge is concave toward the second axis, wherein the acoustic isolator includes a pair of openings oriented about the second axis of the bore, wherein at least a portion of the first edge is disposed between the pair of openings; and
   (c) an ultrasonic blade in acoustic communication with the acoustic waveguide such that the ultrasonic transducer is operable to drive the ultrasonic blade to vibrate ultrasonically via the acoustic waveguide.

16. The ultrasonic instrument of claim 15, wherein the acoustic isolator is formed of an elastomeric material.

17. The ultrasonic instrument of claim 15, wherein the pair of openings of the acoustic isolator are aligned with the bore of the acoustic waveguide such that the anchor pin is insertable through the pair of openings in the acoustic isolator and into the bore of the acoustic waveguide.

18. The ultrasonic instrument of claim 15, wherein the bore, the anchor pin, and the acoustic isolator are positioned at a nodal position relative to the first longitudinal axis of the acoustic waveguide.

19. An ultrasonic instrument comprising:
   (a) an ultrasonic transducer;
   (b) an acoustic waveguide in acoustic communication with the ultrasonic transducer, wherein the acoustic waveguide defines a longitudinal axis, wherein the acoustic waveguide comprises:
      (i) a bore extending transversely through the waveguide,
      (ii) an anchor pin, wherein the anchor pin is insertable through the bore and is operable to secure the acoustic waveguide relative to the ultrasonic instrument, wherein the anchor pin includes an overmold layer thereon, and
      (iii) an acoustic isolator, wherein the acoustic isolator is disposed about the acoustic waveguide, wherein the acoustic isolator comprises a first opening extending through the isolator, wherein the opening is configured to receive the anchor pin therethrough, wherein the acoustic isolator is spaced apart from the overmold layer of the anchor pin when the anchor pin is disposed in the bore; and
   (c) an ultrasonic blade in acoustic communication with the acoustic waveguide such that the ultrasonic transducer is operable to drive the ultrasonic blade to vibrate ultrasonically via the acoustic waveguide.

20. The ultrasonic instrument of claim 19, further comprising:
   a mating component, wherein the mating component is sized to receive the acoustic isolator therein, wherein the mating component has an interior surface; and
   wherein the acoustic isolator is sized to uniformly abut the interior surface.

\* \* \* \* \*